United States Patent [19]

Ekström et al.

[11] 3,931,405

[45] Jan. 6, 1976

[54] PENICILLIN ESTERS AND METHODS AND COMPOSITIONS FOR TREATING INFECTIOUS DISEASES

[75] Inventors: Bertil Åke Ekström; Ödön Kálmán Jozsef Kovács; Olof Harald Sjöberg, all of Sodertalje, Sweden

[73] Assignee: Astra Lakemedel Aktiebolag, Sodertalje, Sweden

[22] Filed: Feb. 27, 1973

[21] Appl. No.: 336,213

[30] Foreign Application Priority Data

Mar. 13, 1972 United Kingdom .............. 11691/72

[52] U.S. Cl. .............................................. 424/271
[51] Int. Cl.² ........................................ A61K 31/43
[58] Field of Search .................. 424/271; 260/239.1

[56] References Cited

UNITED STATES PATENTS

| | | | |
|---|---|---|---|
| 3,660,575 | 5/1972 | Frederiksen et al. | 424/271 |
| 3,697,507 | 10/1972 | Frederiksen et al. | 424/271 |

*Primary Examiner*—Jerome D. Goldberg
*Attorney, Agent, or Firm*—Brumbaugh, Graves, Donohue & Raymond

[57] ABSTRACT

Penicillin esters of the formula

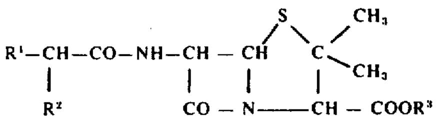

wherein $R^1$ is alkyl containing from one to eight carbon atoms, phenyl, thienyl, furyl, or phenyl substituted with one or more members of the group consisting of halogen, hydroxy, and amino, $R^2$ is selected from the group consisting of $-SO_3H$, tetrazolyl, $-NHSO_2R^4$,

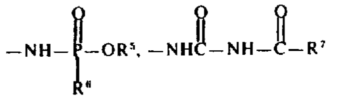

and

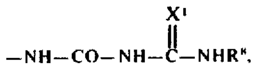

and and wherein $R^3$ is selected from the group consisting of

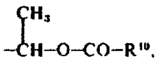

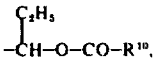

and

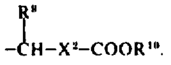

The radicals $R^4$-$R^{10}$, $X^1$ and $X^2$ are defined in the specification. The esters are well resorbed at oral administration.

6 Claims, No Drawings

NEW PENICILLIN ESTERS AND METHODS AND COMPOSITIONS FOR TREATING INFECTIOUS DISEASES

The present invention relates to new penicillin and methods for their preparation. The invention also relates to the preparation of pharmaceutical preparations containing the penicillins and to methods for the pharmacological use of the penicillins.

More precisely this invention relates to mono esters of penicillins of the general formula:

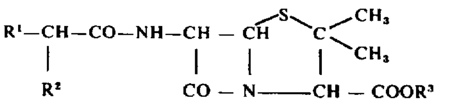

I and therapeutically acceptable salts, in which formula $R^1$ is selected from the group consisting of alkyl groups containing from one to eight carbon atoms, phenyl, thienyl such as 2-thienyl and 3-thienyl, furyl such as 2-furyl 3-furyl, and phenyl substituted with one or more members of the group consisting of halogen, hydroxy and amino;

$R^2$ is selected from the group consisting of $-SO_3H$,

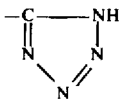

$-NHSO_2R^4$,

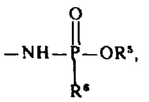

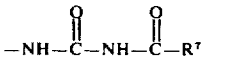

and

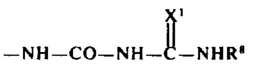

in which radicals $R^4$ is selected from the group consisting of hydroxy, benzyl, and benzyl substituted with one or more halogen;

$R^5$ is selected from the group consisting of hydrogen, alkyl groups containing from one to six carbon atoms, phenyl, and benzyl;

$R^6$ is selected from the group consisting of $—O—R^5$, wherein $R^5$ has the meaning specified above, alkyl groups containing from one to six carbon atoms, phenyl and benzyl;

$R^7$ is selected from the group consisting of alkyl groups containing from one to eight carbon atoms, alkenyl groups containing from two to eight carbon atoms, aryl, aralkyl, and heterocyclic groups, whereby the alkyl, alkenyl, aryl, aralkyl and heterocyclic groups may be substituted with one or more members of the group consisting of halogen, alkyl groups containing from one to three carbon atoms, alkoxy groups containing from one to three carbon atoms, and nitro;

$R^8$ is selected from the group consisting of hydrogen and alkyl groups containing from one to six carbon atoms; and $X^1$ is selected from the group consisting of —O— and —NH—; and $R^3$ is selected from the group consisting of

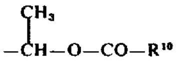

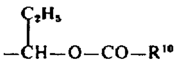

and

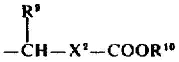

in which formulas $X^2$ is selected from the group consisting of —NH— and —O—;

$R^9$ is selected from the group consisting of H, $—CH_3$ and $—C_2H_5$;

$R^{10}$ is selected from the group consisting of alkyl groups containing from one to eight carbon atoms, cycloalkyl groups containing from three to seven carbon atoms, aryl, aralkyl, and heterocyclic groups whereby the alkyl, cycloalkyl, aryl, aralkyl and heterocyclic groups may be unsubstituted or substituted with one or more groups selected from the class consisting of amino groups, substituted amino groups such as methylamino, diethylamino or acetamido groups, nitro, azido, alkoxy groups containing from one to four carbon atoms, and aralkoxycarbonylamino groups.

Illustrative examples of radicals included in the definitions given above are:

alkyl: methyl, ethyl, propyl, isopropyl, butyl, isobutyl, pentyl, hexyl, heptyl, octyl, 2-ethyl-hexyl cycloalkyl: cyclopropyl, cyclobutyl, cyclopentyl, cyclohexyl, cycloheptyl alkoxy: methoxy, ethoxy, propyloxy, isopropyloxy, butoxy, isobutoxy halogen: F, Cl, Br alkenyl: allyl, propenyl aryl: phenyl, naphtylmethyl aralkyl: benzyl, naphtylmethyl heterocyclic groups:

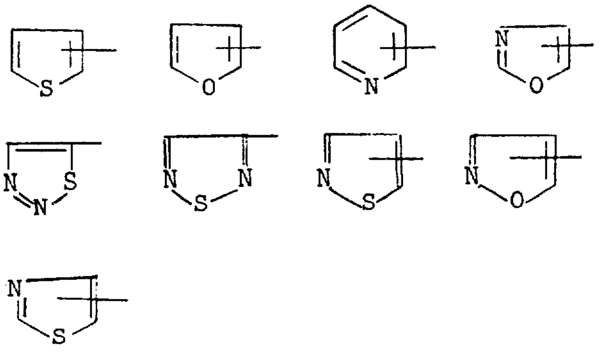

The above illustrative examples of radicals illustrate, where applicable, all the radicals $R^1$–$R^{10}$ to the extent of the definition given to each radical and within the boundaries with regard to number of carbon atoms which may be prescribed for each radical. The compounds of the invention are of value in the treatment of infectious diseases in man or animals caused by bacterial organisms. They may be isolated and used as such but also, depending on the presence of basic or acidic groups in the molecule, in the form of salts with pharmaceutically acceptable organic or inorganic acids or bases. Examples of suitable acids are hydrochloric acid, hydrobromic acid, sulphuric acid, phosphoric acid, acetic acid, tartaric acid, citric acid, and fumaric acid. Examples of suitable bases are sodium hydroxide, potassium hydroxide, calcium hydroxide, aluminium hydroxide, ammonium hydroxide, non-toxic amines as trialkylamines, including triethylamine, procaine, dibenzylamine, N-benzyl-beta-phenethylamine, 1-ephanamine, N,N¹-dibenzylethylenediamine, dehydroabiethylamino, N,N¹-bis-dehydroabietylethylenediamine, N-(lower)-alkylpiperidine (e.g N-ethyl-piperidine) and other bases which have been used for the preparation of salts with penicillins.

The side chain of the penicillin structure in formula I contains an asymmetric carbon atom in the α-position. Depending on the configuration around this carbon atom the compound will occur in two different diastereoisomeric forms which are both biologically active. Likewise the ester groups may contain asymmetric atoms, e.g. when $R^9 = CH_3$ or $C_2H_5$, giving rise to different diasteroisomeric forms which also all are biologically active. It is to be understood that the invention comprises the pure diasteroisomers as well as mixtures of them.

It is known that penicillins of the general structure (IA):

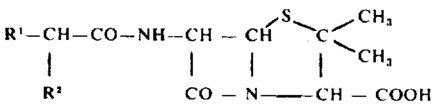

IA or salts thereof, where $R^1$ and $R^2$ are as defined above, have good antibacterial activity against grampositive and gramnegative bacteria, including *Pseudomonas aeruginosa* (Neth. Pat. No. 69 016 46; Neth. Pat. No. 68 18 057; Neth. Pat. No. 69 08 909; U.S. Pat. No. 34 81 922; U.S. Pat. No. 3 479 339; U.S. Pat. No. 3 483 188; U.S. Pat. No. 3 579 501; Swed. Pat. Appl. No. 6667/71; 6668/71.)

Compounds of the general formula IA are, however, poorly absorbed when administered orally and the compounds have in general to be given by injection. It is one purpose of the present invention to provide esters of these compounds, which are well absorbed orally and then hydrolysed within the body to give blood and organ levels of the compounds of the general formula IA that are adequate for the treatment of infectious diseases, caused by bacteria sensitive to penicillins of the general formula IA. To achieve the full antibacterial activity of the penicillins with general formula IA it is necessary to choose such ester groups that are rapidly hydrolysed in vivo under release of the penicillins with the general formula IA. It is an essential feature of the present invention to provide such ester groups that are rapidly hydrolysed in the body after oral absorption.

Said compounds having the formula I are well tolerated, give low frequency of side-effects and may readily be used in pharmaceutical preparations, either as such or in the form of their salts, and they can be intermixed with solid carriers or adjuvants or both. In such preparations the ratio between the therapeutic substance and the carriers and adjuvants may vary between 1 % and 95 %. The preparation may either be processed to for instance tablets, pills or dragees or can be supplied to medical containers, such as capsules or as regards mixtures they can be filled on bottles. Pharmaceutically acceptable, organic or inorganic, solid or liquid carriers may be used, suitably for oral or enteral administration or for topical application, in manufacturing the preparations. Gelatine, lactose, starch, magnesium stearate, talc, vegetabilic and animalic fats and oils, vegetabilic rubber and polyalkylene glycol and other known carriers for pharmaceuticals are all suitable for manufacturing preparations of said compounds. The preferred salt of the compounds of the invention is the hydrochloride, but salts with other inorganic or organic acids, also antibiotically active acids, may be used, for instance phosphates, acetates or salts with phenoxymethylpenicillin. Moreover the preparation may contain other pharmaceutical active components, being suitably administratable together with the compounds of the invention when treating infectious diseases. For instance other suitable antibiotical substances, e.g. gentamycin and polymyxin.

In the treatment of bacterial infections in man, the compounds of the invention are for example administered in amounts corresponding to 5 to 100 mg/kg/day, preferably in the range of 10 to 100 mg/kg/day in divided dosages, e.g. two, three or four times a day. They are administered in dosage units containing e.g. 175, 350, 500 and 1,000 mg of the compounds.

Suitable and preferred classes of the compounds of the invention are obtained by selecting in the compounds of formula I, $R^1$ from a group of phenyl, 2- or 3-thienyl or 2- or 3-furyl, $R^2$ from a group consisting of $SO_3H$, 5-tetrazolyl, benzylsulphonylamino, hydroxysulphonylamino, methoxy (hydroxy) phosphinylamino, hydroxy (phenyl) phosphinylamino, hydroxy (pentyl) phosphinylamino, (lower) acylureido, benzoylureido, guanylureido, 2- or 3-furoylureido, 2- or 3-thineylureido, and $R^3$ from a group consisting of lower alkoxycarbonyloxymethyl, 1'-lower alkoxycarbonyloxy-ethyl, 1'-lower alkoxycarbonyloxy-propyl, lower alkoxycarbonylaminomethyl, 1'-lower alkoxycarbonylamino-ethyl, 1'-lower alkoxycarbonylamino-propyl, 1'-lower acyloxy-ethyl, 1'-lower acyloxy-propyl, phenoxycarbonyloxymethyl, 5-indanyloxycarbonyloxymethyl, 1'-phenoxycarbonyloxy-ethyl, 1'-(5-indanyloxy)carbonyloxy-ethyl, 1'-benzoyloxy-ethyl, 1'-benzoyloxy-propyl.

Still further classes of preferred compounds are obtained by substituting the acyloxy moieties or the alkoxycarbonyloxy, the acyloxycarbonyloxy-, the alkyloxycarbonylamino or the acyloxycarbonylamino groups in $R^1$ and $R^2$ with amino, methylamino or di(-lower)alkyl groups.

Examples of suitable and preferred compounds of the invention are given in Table 1 below.
Table 1
Examples of preferred compounds according to the invention
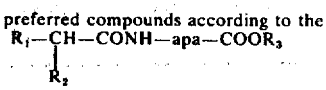
| $R_1$ | $R_2$ | $R_3$ |
|---|---|---|
| $C_6H_5-$ | $-SO_3H$ | 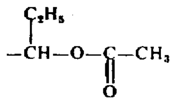 |
| $C_6H_5-$ | 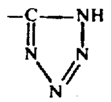 | 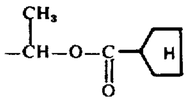 |
| $C_6H_5-$ | $-NH-SO_2CH_2C_6H_5$ | 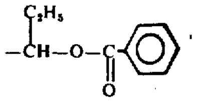 |
| $C_6H_5-$ | $-NH-SO_2-CH_2-C_6H_5$ | 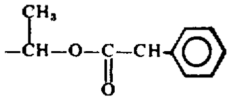 |
| $C_6H_5-$ | 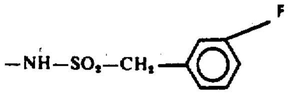 | 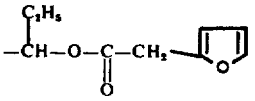 |
| $C_6H_5-$ | 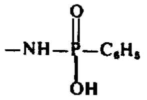 | 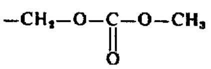 |
| $C_6H_5-$ | 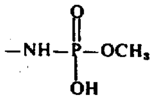 | 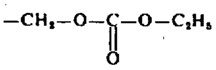 |
| $C_6H_5-$ | 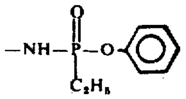 | 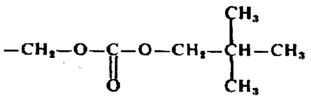 |
| $C_6H_5-$ | 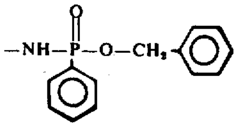 | 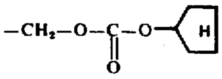 |
| $C_6H_5-$ | 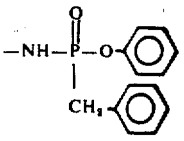 | 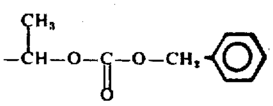 |
| $C_6H_5-$ | 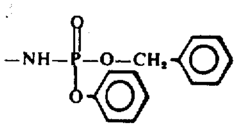 | 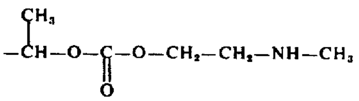 |
| $C_6H_5-$ | 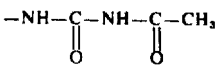 | 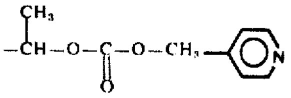 |

Table 1-continued
Examples of preferred compounds according to the invention
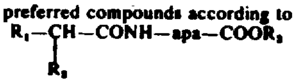
| $R_1$ | $R_2$ | $R_3$ |
|---|---|---|
| $C_6H_5$ — | 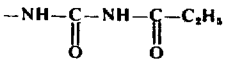 | 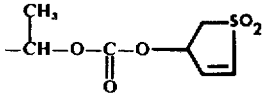 |
| $C_6H_5$— | 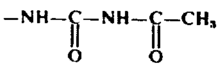 | 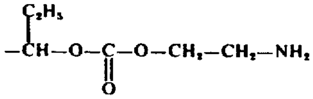 |
| $C_6H_5$— | 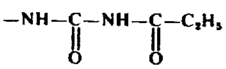 | 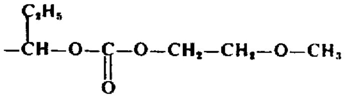 |
| $C_6H_5$— | 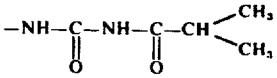 | 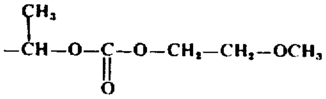 |
| $C_6H_5$— | 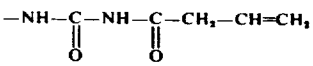 | 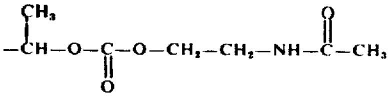 |
| $C_6H_5$— | 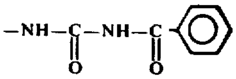 | 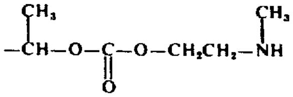 |
| $C_6H_5$— | 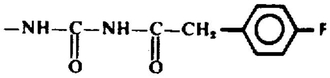 | 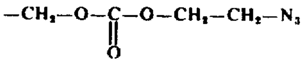 |
| $C_6H_5$— | 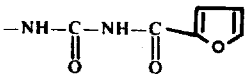 | 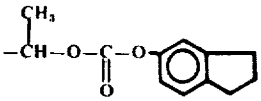 |
| $C_6H_5$— | 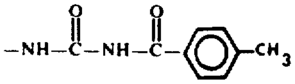 | 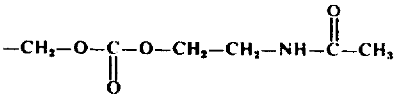 |
| $C_6H_5$— | 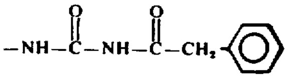 | 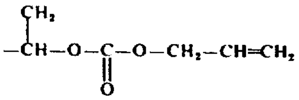 |
| $C_6H_5$— | 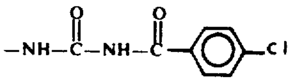 | 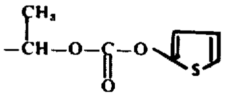 |
| $C_6H_5$— | 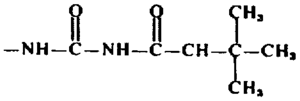 | 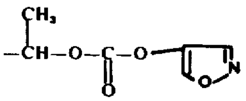 |
| $C_6H_5$— | 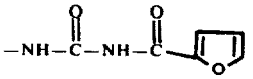 | 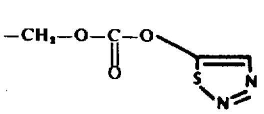 |

Table 1-continued
Examples of preferred compounds according to the invention
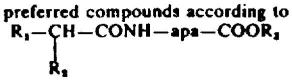
| $R_1$ | $R_2$ | $R_3$ |
|---|---|---|
| $C_6H_5-$ | 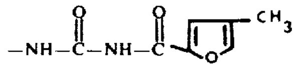 | 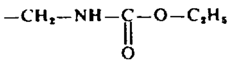 |
| $C_6H_5-$ | 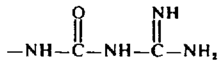 | 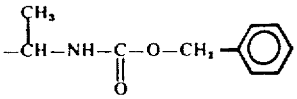 |
| $C_6H_5-$ | 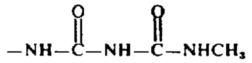 | 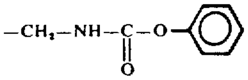 |
| $C_6H_5-$ | 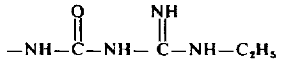 | 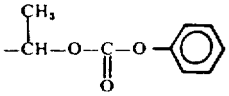 |
| $C_6H_5-$ | 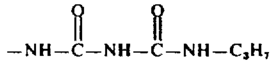 | 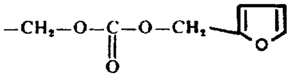 |
| $C_6H_5-$ | $-SO_3H$ | 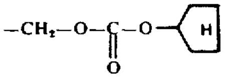 |
| $C_6H_5-$ | $-SO_3H$ | 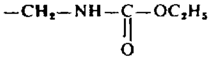 |
| $C_6H_5-$ | $-SO_3H$ | 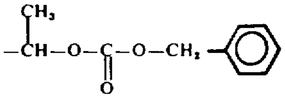 |
| $C_6H_5-$ | 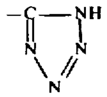 | 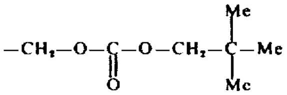 |
| $C_6H_5-$ | 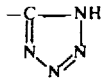 | 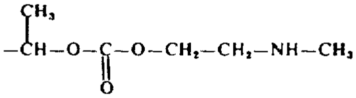 |
| $C_6H_5-$ | 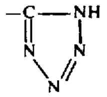 | 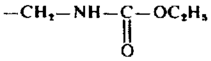 |
| $C_6H_5-$ | 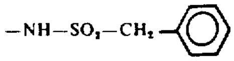 | 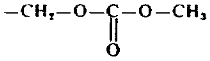 |
| $C_6H_5-$ | 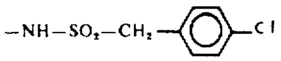 | 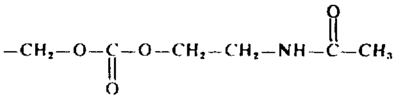 |
| $C_6H_5-$ | 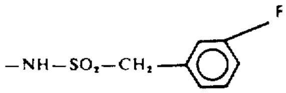 | 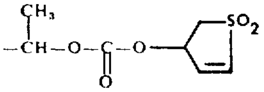 |

Table 1-continued
Examples of preferred compounds according to the invention
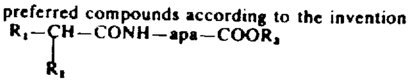
| $R_1$ | $R_2$ | $R_3$ |
| --- | --- | --- |
| $C_6H_5$— | 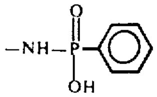 | 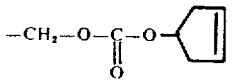 |
| $C_6H_5$— | 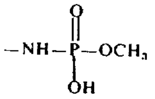 | 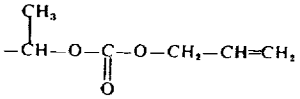 |
| $C_6H_5$— | 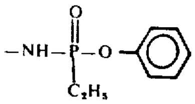 | 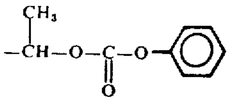 |
| $C_6H_5$— | 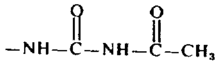 | 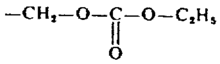 |
| $C_6H_5$— | 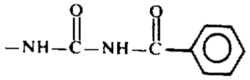 | 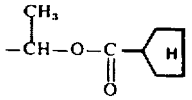 |
| $C_6H_5$— | 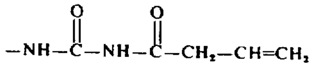 | 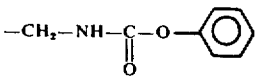 |
| 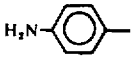 | $SO_3H$ | 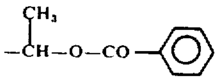 |
| 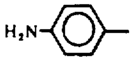 | 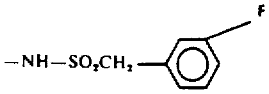 | 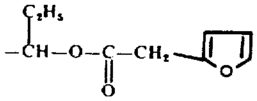 |
| 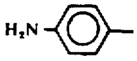 | 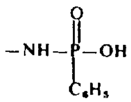 | 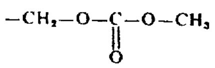 |
| 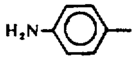 | 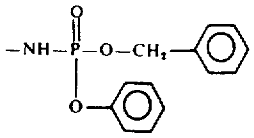 | 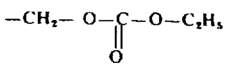 |
| 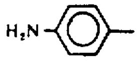 | 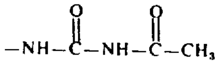 | 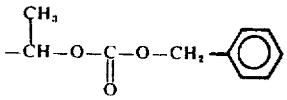 |
| $C_6H_5$— | 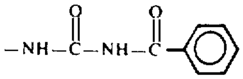 | 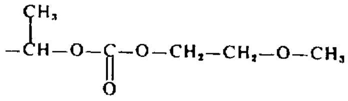 |
| $C_6H_5$— | 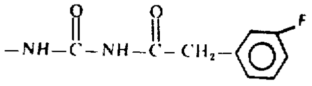 | 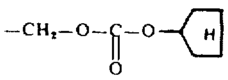 |

Table 1-continued
Examples of preferred compounds according to the invention
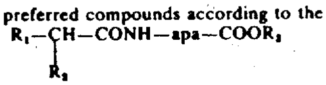
| $R_1$ | $R_2$ | $R_3$ |
|---|---|---|
| $C_6H_5$— | 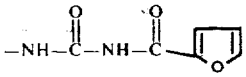 | 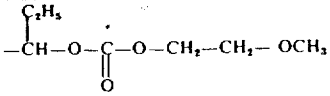 |
| $C_6H_5$— | 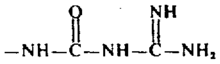 | 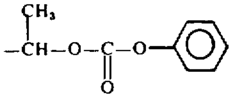 |
| $C_6H_5$— | 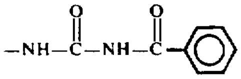 | 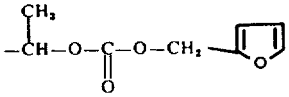 |
| 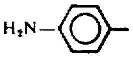 | 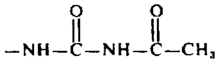 | 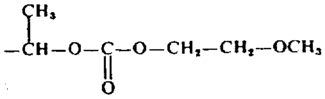 |
| 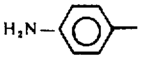 | 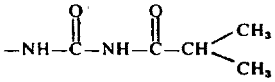 | 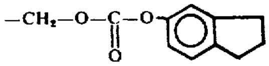 |
| 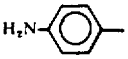 | 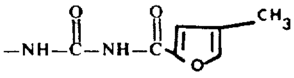 | 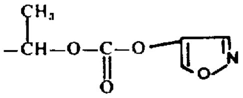 |
| 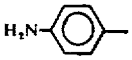 | 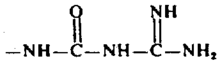 | 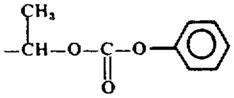 |
| 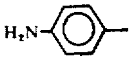 | 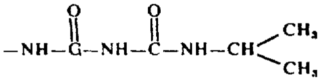 | 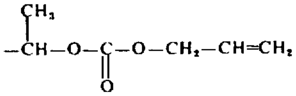 |
| 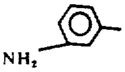 | 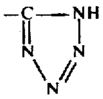 | 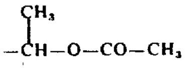 |
| 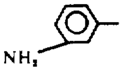 | 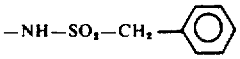 | 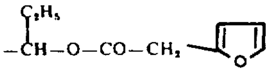 |
| 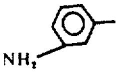 | 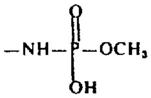 | 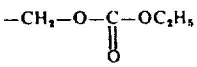 |
| 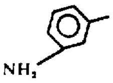 | 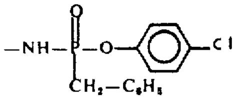 | 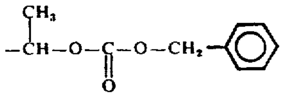 |
| 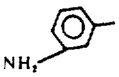 | 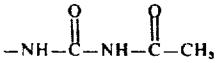 | 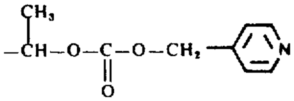 |

Table 1-continued
Examples of preferred compounds according to the invention
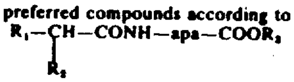
| $R_1$ | $R_2$ | $R_3$ |
| --- | --- | --- |
| 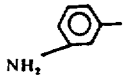 | 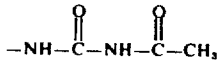 | 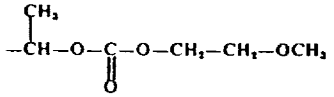 |
| 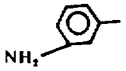 | 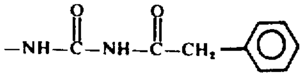 | 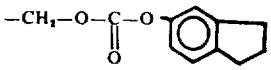 |
| 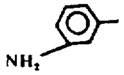 | 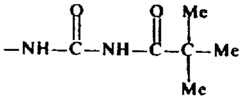 | 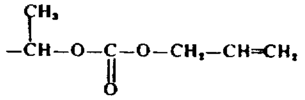 |
| 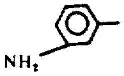 | 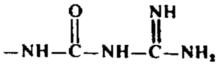 | 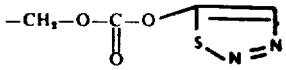 |
| 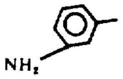 | 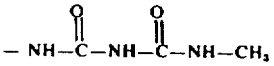 | 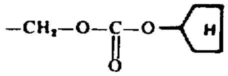 |
| 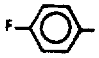 | 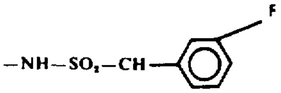 | 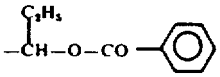 |
| 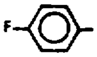 | 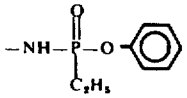 | 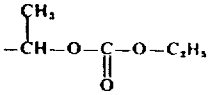 |
| 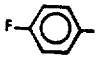 | 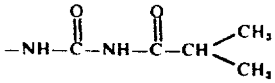 | 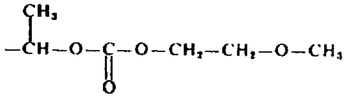 |
| 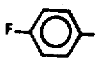 | 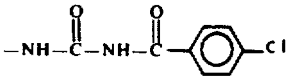 | 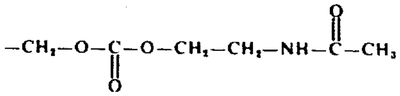 |
| 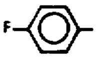 | 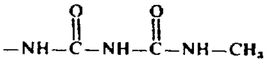 | 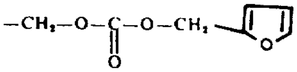 |
| 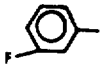 | 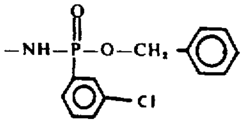 | 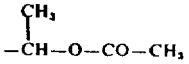 |

Table 1-continued
Examples of preferred compounds according to the invention
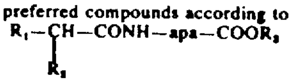
| $R_1$ | $R_2$ | $R_3$ |
|---|---|---|
| 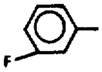 | 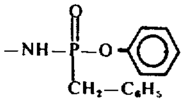 | 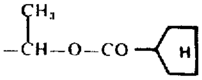 |
| 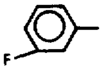 | 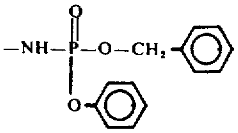 | 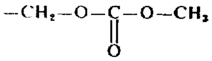 |
| 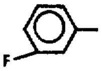 | 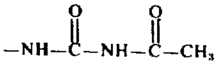 | 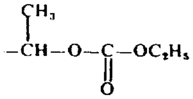 |
| 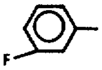 | 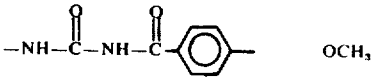 | 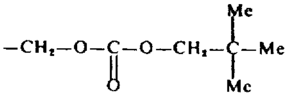 |
| 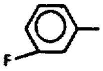 | 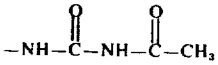 | 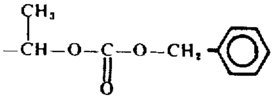 |
| 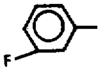 | 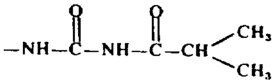 | 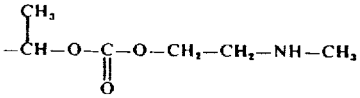 |
| 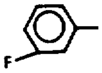 | 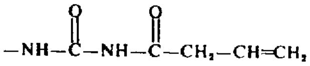 | 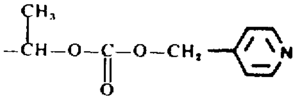 |
| 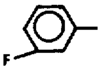 | 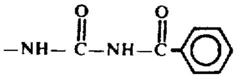 | 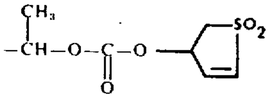 |
| 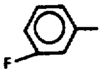 | 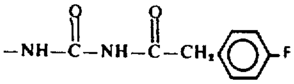 | 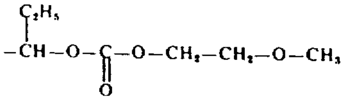 |
| 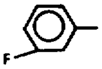 | 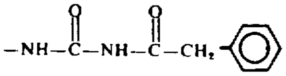 | 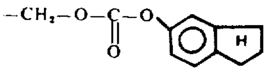 |
| 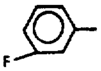 | 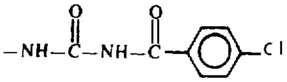 | 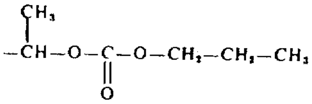 |
| 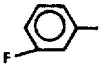 | 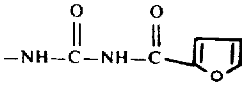 | 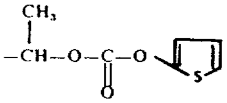 |

Table 1-continued
Examples of preferred compounds according to the invention
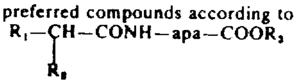
| $R_1$ | $R_2$ | $R_3$ |
| --- | --- | --- |
| 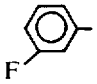 | 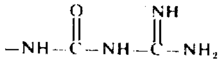 | 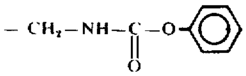 |
| 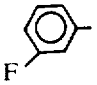 | 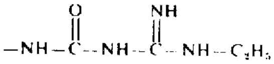 | 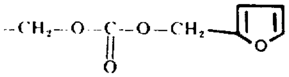 |
| 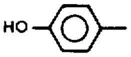 | 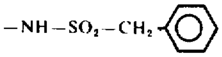 | 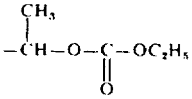 |
| 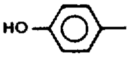 | 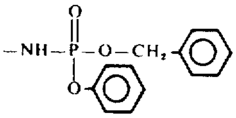 | 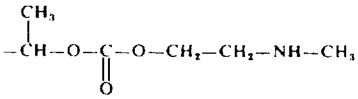 |
| 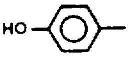 | 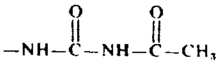 | 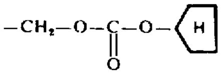 |
| 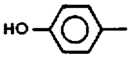 | 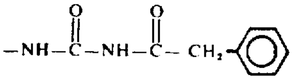 | 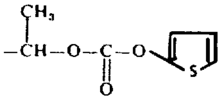 |
| 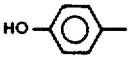 | 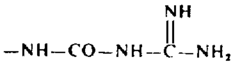 | 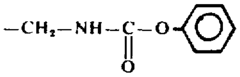 |
| 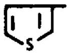 | $-SO_3H$ | 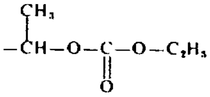 |
| 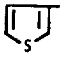 | 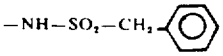 | 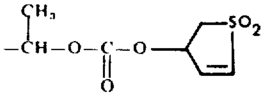 |
| 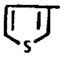 | 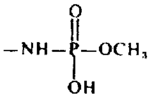 | 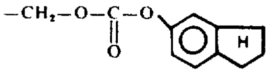 |
| 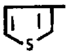 | 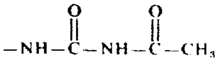 | 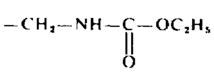 |
| 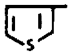 | 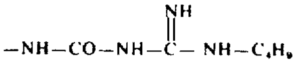 | 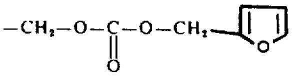 |
| 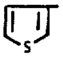 | $-SO_3H$ | 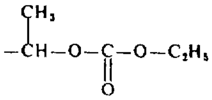 |

Table 1-continued
Examples of preferred compounds according to the invention
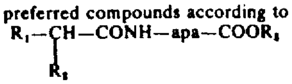
| $R_1$ | $R_2$ | $R_3$ |
|---|---|---|
| 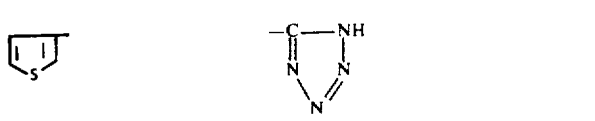 | | 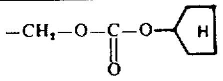 |
| 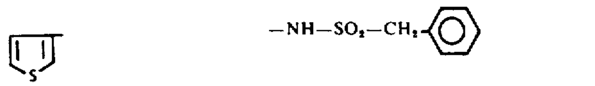 | | 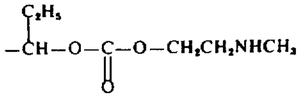 |
| 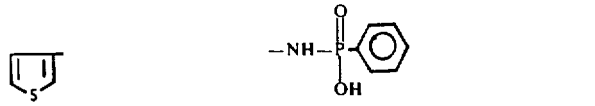 | | 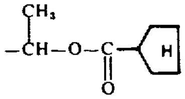 |
| 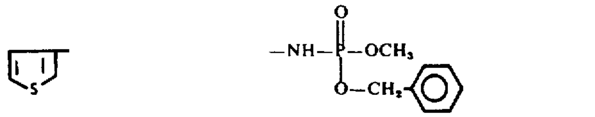 | | 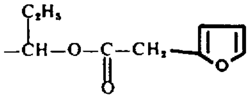 |
| 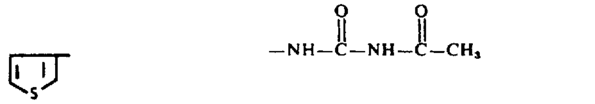 | | 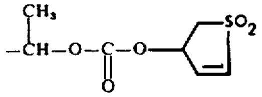 |
| 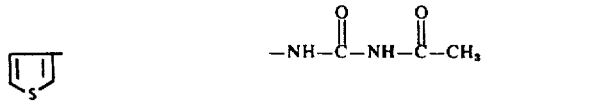 | | 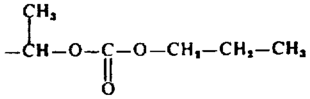 |
| 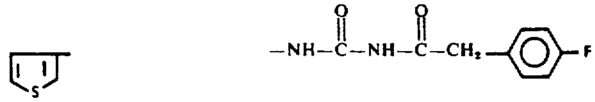 | | 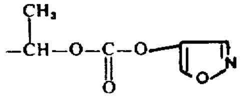 |
| 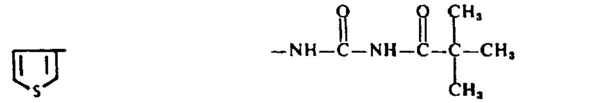 | | 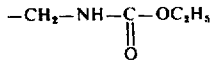 |
| 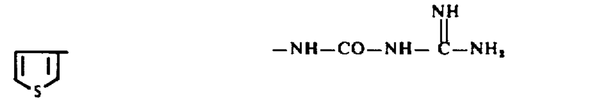 | | 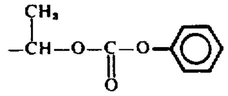 |
| 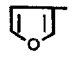 | $-SO_3H$ | 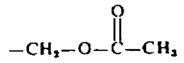 |
| 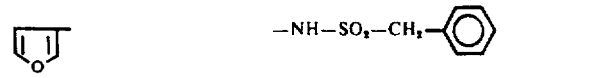 | | 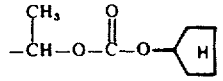 |
| 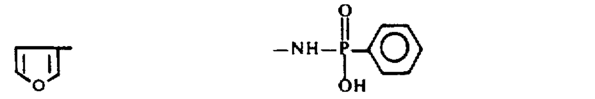 | | 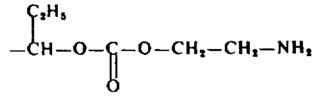 |
| 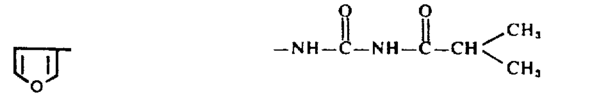 | | 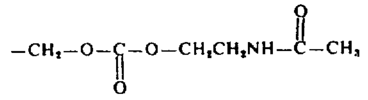 |
| 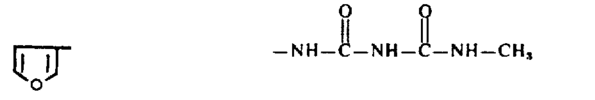 | | 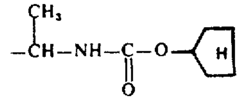 |
| 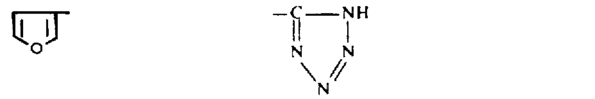 | | 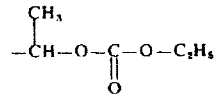 |

Table 1-continued

Examples of preferred compounds according to the invention

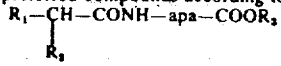

| $R_1$ | $R_2$ | $R_3$ |
|---|---|---|
| 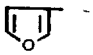 | 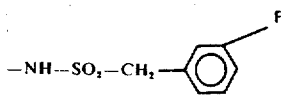 | 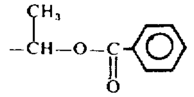 |
| 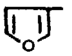 | 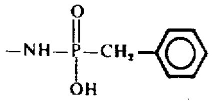 | 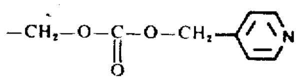 |
| 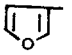 | 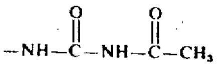 | 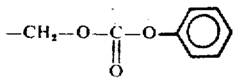 |
| 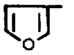 | 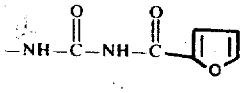 | 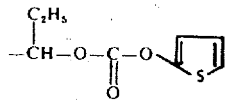 |

The compounds of the invention are prepared by different methods.

Method A

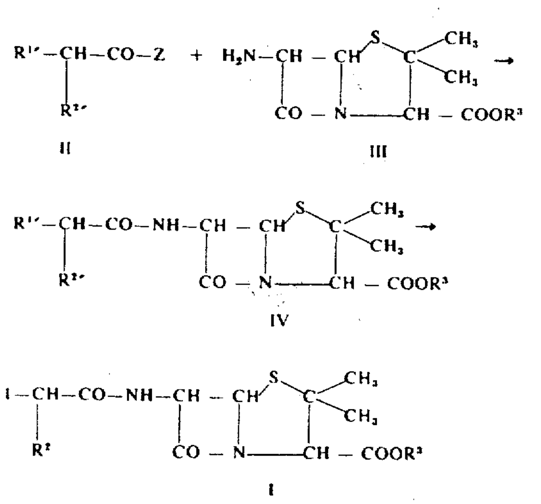

II III IV I

According to this method an activated carboxylic acid derivative II where $R^{1'}$ is $R^1$, defined above, or, when $R^1$ contains an amino or hydroxy group, a protected derivative of $R^1$, and $R^{2'}$ is either $R^2$, defined above, or in case $R^2$ contains an amino or hydroxy group a protected derivative of $R^2$, and COZ is a reactive group capable of reacting with an amino group under formation of an amide moiety, e.g. an acid chloride or its functional equivalent, is brought to react with an ester of 6- aminopenicillanic acid (III) where $R^3$ is as defined above, under formation of a penicillin ester IV.

When $R^{1'} = R^1$ and $R^{2'} = R^2$ the product is a compound of the invention. When $R^{1'}$ or $R^{2'}$ contain amino or hydroxy groups that are protected, the protecting group is removed in at least one additional step to give the compounds of the general formula I. As protecting groups for the amino and hydroxy groups such protecting groups can be used that can be removed without destruction of the penicillin ring system. Such protecting groups known to the art are e.g. the benzyloxycarbonyl group which can be removed by catalytic hydrogenation, the o-nitrophenylsulfenyl group which can be removed by treatment with nucleophilic agents at acid pH (Jap. Pat. 505 176), the α-p-tolylsulphonyl-ethoxycarbonyl group which can be removed in basic agents such as sodium thiophenoxide, the β-trichloroethoxycarbonyl group which can be removed with zink in acetic acid, and the 1-methoxycarbonylpropen-2-yl group which can be removed by mild acidic treatment, as protecting groups for the amino groups and e.g. the benzyl group, which can be removed by catalytic hydrogenation, as protecting group for the hydroxy group.

The reaction constitutes an acylation of an ester of 6-aminopenicillanic acid and can be performed in the manner described for acylation of other ester of 6-aminopenicillanic acid (e.g. in Fr. Pat. No. 1 576 027). The acylating group -CO-Z in the compound II may be an acid chloride group, or a group functioning in the same way, e.g. an acid bromide, an acid azide, an anhydride, a mixed anhydride formed with an inorganic acid or an organic acid and especially with an alkoxyformic acid.

The compound II may also be a derivative obtained by reaction between a carboxylic acid of the formula

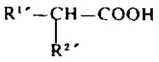

wherein $R^{1'}$ and $R^{2'}$ have the meaning specified above, and a carbodiimide or other compounds functioning in the same way such as N,N$^1$-carbonyldiimidazole, N-ethyl-5-phenylisoxazolium-3'-sulphonate or N-tert.butyl-5-methylisoxazolium perchlorate.

The reaction can be performed in organic solvents like diethylether, tetrahydrofuran, acetone, ethyl acetate, chloroform, methylene chloride, dimethylformamide, dimethyl sulfoxide, or hexamethylphosphoramide, in water or in aqueous organic solvents in presence of organic or inorganic bases like triethylamine, quinoline, pyridine, N-methyl-morpholine, sodium hydroxide, sodium bicarbonate or potassium carbonate.

The compound of the general formula IV may be isolated by extraction from the reaction mixture, if necessary after dilution with water and neutralization.

The esters of 6-aminopenicillanic acid with the general structure III may be prepared by treatment of 6-APA with compounds $R^3$—Y (V) where $R^3$ has the same meaning as above and Y is halogen or a functionally equivalent group capable of reacting with a carboxy group under formation of an ester linkage, such as a sulphonic acid residue. The reaction is preferably performed in organic solvents like dimethylformamide or dimethylsulphoxide. When $R^3$ in the final product of formula I contains a primary amino group such a primary amino group may need to be protected by a suitable protecting group during the reaction between 6-APA and $R^3$—Y. Suitable protecting groups are for example the groups mentioned in connection with $R^{1\prime}$ and $R^{2\prime}$ above.

Alternatively 6-acylaminopenicillanic acids with acyl groups that can be removed without destruction of the penicillin ring system are treated with $R^3$—Y to give esters of the 6-acylamino penicillanic acids from which the acyl groups then are removed to give the esters of 6-aminopenicillanic acid of the formula III. A preferred method consists of reacting a salt, e.g. the sodium or potassium salt of benzylpenicillin, with $R^3$—Y in an organic solvent like acetone, methylethylketone, chloroform, methylenechloride, dimethylformamide, dimethylsulphoxide or hexamethylphosphoramide or in a mixture of an organic solvent and water, e.g. aqueous acetone or dioxane, to give the corresponding ester of benzylpenicillin. The phenylacetyl side chain is then removed according to the method described in Neth. Pat. No. 6,401,421 or South African Pat. No. 67/2927 by treatment with phosphorous pentachloride in presence of a tertiary organic base to give an imino chloride which is reacted with an alcohol like propanol to give the corresponding imino ether which is hydrolyzed by addition of water or alcoholized to give the ester III. Alternatively the phenylacetyl side chain may be removed by enzymatic hydrolysis using a *E.coli* acylase according to method described in French Pat. No. 1,576,027. The mixture obtained may if desired be used for direct acylation without isolating the 6-aminopenicillanic acid ester.

In still another method N-protected 6-aminopenicillanic acids are reacted with $R^3$—Y to give the corresponding ester from which the protecting groups are removed to give the compounds of the general formula III. Examples of protecting groups which can be used are the benzyloxycarbonyl group which is removed by catalytic hydrogenation, the o-nitro-phenylsulphenyl group which can be removed by treatment with nucleophilic agents at acid pH (Jap. Pat. No. 505,176) and the trityl group which can be removed by mild acid hydrolysis.

Method B

A natural penicillin of the formula

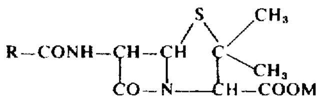

VI where RCO represents the acyl group in the side chain of the natural penicillin and M represents hydrogen or an alcali metal atom such as sodium, potassium, calcium, is esterified by reaction with a compound of the formula $R^3$—Y V where $R^3$ and Y have the meanings specified above, whereafter the ester of the formula

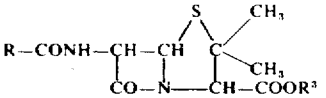

VII thus formed is reacted with a phosphorous halide in an inert solvent and suitably in presence of a tertiary amine to give an imino halide compound, which is reacted with a lower alcohol to give an iminoether derivative, which imino ether thereafter is reacted with a compound of the formula

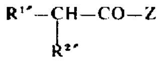

II wherein $R^{1\prime}$, $R^{2\prime}$ and Z have the meanings specified above, and the reaction product treated with water or an alcohol to give a compound of the formula

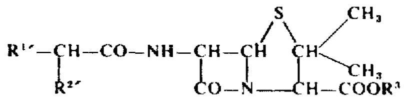

IV which compound thereafter is converted to a compound of the formula I as is described under A above. In this method the intermediate imino ether compound is directly acylated without isolation of any intermediate products.

The group RCO— in the compound of the formula VI is an organic acyl group contained in known natural penicillins. Thus the group R may be an alkyl, cycloalkyl, aryl, aralkyl or heterocyclic group and derivatives thereof. Examples of suitable groups R are heptyl, phenoxymethyl, 2-thienylmethyl, 2-furylmethyl, and benzyl. Examples of suitable phosphorous halides are phosphorous pentachloride, phosphorous pentabromide, phosphorous oxychloride, phosphorous trichloride, etc. Phosphorous pentachloride is preferred. Examples of suitable alcohols with which the imino halide may be treated are lower alkyl alcohols such as methanol, ethanol, and n-propanol.

Method C

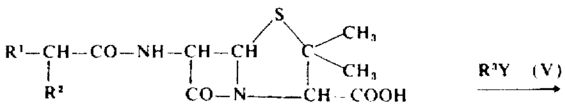

VIII

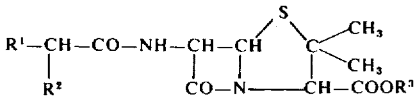

I

Penicillins with the formula V, where $R^1$ and $R^2$ are defined above are prepared by acylation of 6-aminopenicillanic acid according to known methods. Treatment of the penicillins with the formula VIII with a compound $R^3-Y$ V where $R^3$ is as defined above and Y is halogen preferably chlorine, bromine or iodine or a functionally equivalent group capable of reacting with the carboxyl group in the compound of the formula IV under formation of an ester linkage, such as a sulphonic acid residue, gives the compounds of the invention (I).

The reaction is preferably performed with a salt, e.g. a sodium, potassium, calcium or a trialkylammmonium salt or a tetraalkyl-ammonium salt, preferably the tetrabutylammonium salt, of the compound VIII in an organic solvent like acetone, tetrahydrofurane, chloroform, methylene chloride, dimethylformamide, dimethylsulphoxide or hexamethylphosphoramide or in a mixture of water and an organic solvent, e.g. aqueous dioxane or acetone. When the reaction is carried out using a tetraalkylammonium salt, the solvent is preferably chloroform, methylenechloride or acetone.

D. for preparation of derivatives of α-aminopenicillins of the formula

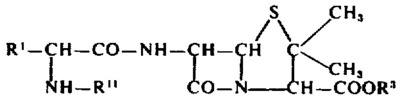

IX wherein $R^1$ and $R^3$ have the meaning specified above and $R^{11}$ is a member of the group consisting of $R^{15}-SO_2-$ and 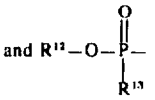

wherein $R^{15}$ is selected from the group consisting of benzyl and benzyl substituted with one or more halogen;

$R^{12}$ is selected from the group consisting of alkyl groups containing from 1 to 6 carbon atoms, unsubstituted phenyl, and unsubstituted benzyl; and wherein $R^{13}$ has the meaning specified above for $R^6$; reacting a compound of the formula

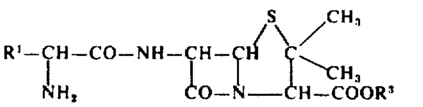

X wherein $R^1$ and $R^3$ have the meaning specified above, with a compound of the formula $R^{11}-Cl$ XI wherein $R^{11}$ has the meaning specified above; whereafter $R^{12}$ —O— and $R^{13}$ if desired are converted to OH;

E. for preparation of compounds of the formula

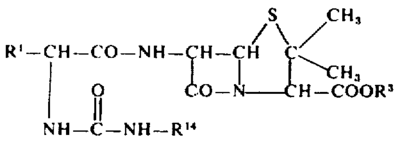

XII wherein $R^1$ and $R^3$ have the meaning specified above and $R^{14}$ is

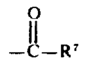

or

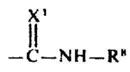

wherein $X^1$, $R^7$ and $R^8$ have the meaning specified above; reacting a compound of the formula

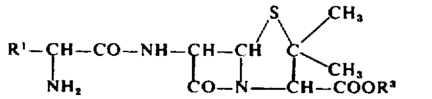

X wherein $R^1$ and $R^3$ have the meanings specified above, with a compound of the formula $R^{14}-N=C=O$ XIII F. for preparation of compounds of the formula

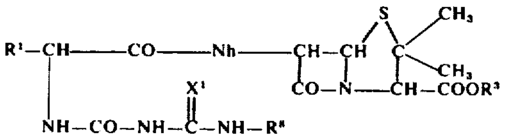

XIV wherein $R^1$, $R^3$, $R^8$, and $X^1$ have the meanings specified above; reacting a compound of the formula

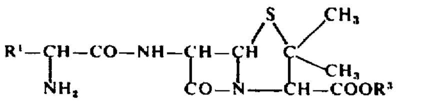

X wherein $R^1$ and $R^3$ have the meanings specified above, with a carbamoylating agent obtained by treatment of a compound of the formula

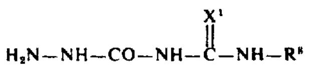

XV wherein $X^1$ and $R^8$ have the meaning specified above with nitrous acid or a source thereof or an oxidizing agent such as iodine or equivalents thereof such as sodium hypochlorite or hypochlorous acid or chlorine.

G. for preparation of compounds of the formula

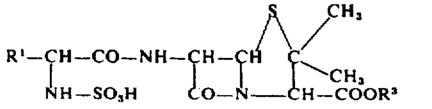

XVI wherein $R^1$ and $R^3$ have the meaning specified above; reacting a compound of the formula

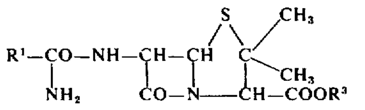

X wherein $R^1$ and $R^3$ have the meaning specified above, with a sulphate-trioxidetri (lower) alkylamine complex such as trimethylamine complex;

whereafter the compound obtained, if desired, is converted into a therapeutically acceptable salt. The reaction D is carried out in organic solvents like diethyl ether, acetone, tetrahydrofuran, chlorofrom, methylene chloride, dimethylformamide, dimethylsulphoxide or hexamethylphosphoramide, or in water, or in mixtures of water and organic solvents, e.g. aqueous acetone or dioxane, if necessary in presence of acid binding agents like inorganic bases or tertiary organic bases.

The use described in Method C of tetraalkylammonium salts of a penicillin is not previously described in the penicillin literature. It is a new method of preparing penicillin ester. In this method the preferred tetraalkylammonium salt is the tetrabutylammonium salt, and the preferred solvents are chloroform, methylenechloride or acetone. Also 6-APA can be esterified in the same way using a tetraalkylammonium salt of 6-APA.

As described above the starting material may be in the form of a salt, for instance a sodium, potassium, calcium or trialkylammonium salt, in some of the ways for the preparation of the compounds of the invention.

In addition, tetraalkylammonium salts and other analogues salts such as salts where the cation has the formula $A^1A^2A^3A^4N^+$ in which formula $A^1$ is selected from the group consisting of straight and branched alkyl groups containing from three to six carbon atoms, substituted and unsubstituted aryl, and substituted and unsubstituted aralkyl, and wherein $A^2$, $A^3$ and $A^4$, which are the same or different, are selected from the group consisting of straight and branched alkyl groups containing from one to six carbon atoms, provided that $A^2$, $A^3$ and $A^4$ are alkyl with 3–6 carbon atoms when $A^1$ is alkyl, may be used.

Illustrative examples of suitable combinations of $A^1$, $A^2$, $A^3$ and $A^4$ in the quaternary ammonium ion $A^1A^2A^3A^4N^+$ are given below:

Table I

Examples of suitable combinations of the radicals $A^1$—$A^4$ in the $A^1A^2A^3A^4N^+$ ion

| $A^1$ | $A^2$ | $A^3$ | $A^4$ |
|---|---|---|---|
| n-propyl | n-propyl | n-propyl | n-propyl |
| i-propyl | i-propyl | i-propyl | i-propyl |
| n-butyl | n-butyl | n-butyl | n-butyl |
| i-butyl | i-butyl | i-butyl | i-butyl |
| n-pentyl | n-pentyl | n-pentyl | n-pentyl |
| n-hexyl | n-hexyl | n-hexyl | n-hexyl |
| phenyl | methyl | methyl | methyl |
| phenyl | ethyl | ethyl | ethyl |
| p-tolyl | ethyl | ethyl | ethyl |
| p-chlorophenyl | ethyl | ethyl | ethyl |

When the radicals $A^1$–$A^4$ are all different the resulting ion contains an asymmetric centre and may occur in two enantiomeric forms. Epimeric forms can occur if $A^1$, $A^2$, $A^3$ and/or $A^4$ contain one or more asymmetric carbon atoms.

Examples of quaternary ammonium ions containing an asymmetric centre are given in Table II below:

Table II

Examples of quaternary ammonium ion $A^1A^2A^3A^4N^+$ containing an asymmetric centre

| $A^1$ | $A^2$ | $A^3$ | $A^4$ |
|---|---|---|---|
| benzyl | n-propyl | i-propyl | n-butyl |
| benzyl | n-propyl | i-propyl | sec.butyl |
| benzyl | n-propyl | n-butyl | sec.butyl |
| n-propyl | n-propyl | n-butyl | sec.butyl |
| n-propyl | n-propyl | n-propyl | sec.butyl |
| n-propyl | n-propyl | n-propyl | sec.pentyl |
| n-propyl | n-propyl | n-propyl | sec-hexyl |
| n-propyl | n-propyl | n-butyl | sec.hexyl |

The use as described above of a quaternary salt form of the starting material for the preparation of the compounds of this invention is not previously described in the literature pertaining to this technical field. In this method the preferred cation is the tetraalkylammonium ion, particularly the tetrabutylammonium ion. The preferred solvents are chloroform, methylenechloride and acetone.

The quaternary ammonium salt form of the above described starting material may be prepared by reacting the starting material in question with a quaternary ammonium salt of the formula $A^1A^2A^3A^4N^+ B^-$ wherein $A^1$, $A^2$, $A^3$ and $A^4$ have the meanings specified above and B is a suitable anion such as $HSO_4^-$, $Cl^-$ or $CH_3COO^-$ to the formation of a quaternary salt of the starting material.

The salts of the formula above which contains B as the anion may be prepared in known manner analogous as described in for instance Belgian Pat. No. 751 791. The anion $B^-$ is in the preferred embodiment $HSO_4^-$.

The following examples will further illustrate the invention.

EXAMPLE I

Preparation of 6-(D-α-Benzylsulfonylamino-phenylacetamido) penicillanic acid 3-(1′-ethoxycarbonyloxyethyl)ester α-Chlorodiethylcarbonate (11.45 g, 75 mM) was added to a stirred and ice-cooled suspension of 6-(D-α-benzylsylfonylamino-phenylacetamido)penicillanic acid sodium salt (13.15 g, 25 mM) and sodium bicarbonate (12.6 g, 150 mM) in 70 % dioxane (50 ml). Stirring was continued at room temperature for 62 hours. The solid material was filtered off and washed with dioxane (2 × 50 ml). The filtrate was evaporated under reduced pressure, the residue was dissolved in ethylacetate (250 ml) and the mixture was washed successively with saturated sodium bicarbonate and sodium chloride solution. After drying, the organic phase was evaporated, and the residue, a heavy oil (4.85 g), was chromatographed on silica gel (100 g) column with isopropyl-ether-acetone (6:4) mixture. The desired product was isolated as a foam (1.37 g, 8,8 %) and it showed only one spot on TLC.

The IR spectrum (KBr disk) had absorption maximum ($cm^{-1}$) at 1780–1770 (β-lactam and ester); 1690 (amide). The NMR spectrum in deuterochloroform showed absorptions at: 7.35 (s, $C_6H_5$); 7.25 (s, $C_6H_5$); 6.70 (q, O<u>CH</u>($CH_3$)O); 5.90 (s, NH $SO_2$); 5.35 (s, 5-H - 6-H); 5.05 (s, CO<u>CH</u>$C_6H_5$); 4.35 (s, 3-H); 4.25 - 4.00 (m, $CH_2SO_2$, O<u>CH₂</u>$CH_3$); 1.60 - 1,15 (m, gem $CH_3$, OCH(<u>CH₃</u>)O, $OCH_2$<u>CH₃</u>.

Analysis: Calculated for $C_{28}H_{33}N_3O_9S_2$ (619,74): C 54.27; H 5.37; N, 6.78; O 23.23; S 10.35.

Found: C 54.70; H 5.43; N 6.65; O 23.02; S 9.92.

The degree of hydrolysis of all penicillin esters described herein was determined in Sörensen's buffer solution (B), in 50 % human serum (H) and in 5 % rat serum (R) in the presence of 10 % dimethylsulfoxide, the pH of each mixture being adjusted to 6,8. The mixtures were incubated at 37°, samples being taken at different intervals. The concentration of the liberated free penicillin was measured by the microbiological cup-plate method and the values in per cent after three (B3 and H3) and one (R1) hours respectively are given. The stability in synthetic gastric acid (G) was established by treating the substance in gastric acid in the presence of 20 % dimethylsulfoxide at 37° for 30 minutes and afterwards the pH was adjusted to 6,8 and the substance was treated with 5 % rat serum at 37° for 1 hour. The "G 0.5" values represent the remaining penicillin ester in per cent of the original amount. The degree of hydrolysis of the substance described in this example was: B3 = 7.4 %; H 3 = 23.3 %; R1 = 98.1; G 0.5 = 60.7 %.

In the same way the following esters were prepared:

6-(D-α-p-toluene sulfonylamino-phenyl acetamido)-
6-(D-α-p-chlorobensenesulfonylamino-phenyl acetamido)- and
6-(D-α-o-methoxybensenesulfonylamino-phenylacetamido) penicillanic acid 3-(1'-ethoxycarbonylethyl)esters.

EXAMPLE II

Preparation of 6-(D-α-Benzylsulfonylamino-α-(3-thienylacetamido) penicillanic acid 3-(1'-ethoxycarbonyloxyethyl) ester To a stirred and ice-cooled mixture of 6-aminopenicillanic acid (3-(1'-ethoxycarbonyloxyethyl)ester p-toluene sulfonate (5.1 g, 10 mM) and dry triethylamine (2.0 g, 20 mM) in dry chloroform (50 ml) was added dropwise α-benzylsulfonylaminothienyl acetyl chloride (3.3 g, 10 mM). Stirring was continued for 1 hour. The organic phase was washed with 0.05 N hydrochloric acid and water. After drying the organic phase was evaporated and the brown oil residue (5,4 g) was chromatographed on silica gel (100 g) column with isopropyletheracetone (6:4) mixture. The desired compound was isolated as a white foam (2,46 g, 39,2 %) from one of the middle fractions of the eluate and showed only one spot on TLC.

IR (KBr): 1770–1760 (β-lactam and ester); 1680 (amide).

NMR ($CDCl_3$): 7.40 - 7.15 (m, $C_6H_5$, thienyl); 6.75 (q, O<u>CH</u>($CH_3$)O); 5.90 (s, NH $SO_2$); 5.35 (s, 5-H - 6-H); 5.05 (s, CO<u>CH</u>(NH)thienyl); 4.35 (s, 3-H); 4.25

- 4.05 (m, $CH_2SO_2O$<u>CH₂</u>$CH_3$); 1.60 - 1.15 (m, gem $CH_3$, OCH(<u>CH₃</u>)O, $OCH_2$<u>CH₃</u>).

Analysis: Calculated for $C_{26}H_{31}N_3O_9S_3$ (625,77): C 49.90; H 4.99; N 6.72; O 23.01; S 15.38.

Found: C 50.08; H 5.03; N 6.58; O 22.88; S 15.32.

Degree of hydrolysis: B3 = 19.5 %; H3 = 26.8 %; R1 = 107.5 %; G 0.5 = 72.1 %.

In the same way 6-(D-α-p-bromo-bensenesulfonylamino-α-(3-thienyl)-acetamido, 6-(D-α-methylsulfonylamino-α-(3-thienyl)-acetamido- and 6-(D-α-p-toluenesulfonylamino-α-(3-thienyl)-acetamido - penicillanic acid 3-(1'-ethoxycarbonylethyl)esters were prepared.

EXAMPLE III

Preparation of 6-(D-α-Benzylsulfonylamino-phenylacetamido) penicillanic acid 3-(ethoxycarbonyloxymethyl)ester To a stirred suspension of 6-(D-α-benzylsulfonylaminophenylacetamido) penicillanic acid potassium salt (5.95 g, 11 mM) and dry dimethylsulfoxide (11 ml) was added dropwise chloromethylethylcarbonate (1.53 g, 11 mM). Stirring was continued at room temperature for 2 hours.

The mixture was poured into an ice-cooled 0,5 N sodium bicarbonate solution (90 ml) and the mixture was extracted with ethyl acetate (2 × 90 ml). The combined organic phase was washed with cold 0,5 N sodium bicarbonate solution and cold water. After drying the organic phase was evaporated, and the yellow foam (5.1 g) was chromatographed on silica gel (100 g) column with isopropylether-acetone (6:4) mixture. The desired product was isolated as a foam (3.15 g, 47 %) and it showed only one spot on TLC.

IR (KBr): 1790–1770 (β-lactam and ester); 1690 (amide).

NMR ($CDCl_3$): 7.35 (s, $C_6H_5$); 7.25 (s, $C_6H_5$); 5.95 (s, NH $SO_2$) 5.75 (s, $OCH_2O$); 5.40 (s, 5-H - 6-H); 5.05 (s, CO<u>CH</u>$C_6H_5$); 4.40 (s, 3-H); 4.30 - 4.05 (m, $CH_2SO_2$, O<u>CH₂</u>$CH_3$); 1.45 -1.15 (m, gem $CH_3$, $OCH_2$<u>CH₃</u>).

Analysis: Calculated for $C_{27}H_{31}N_3O_9S_2$ (605.72: C 53.54; H 5.16; N 6.94; O 23.77; S 10.59.

Found: C 53.84; H 5.27; N 6.80; O 23.38; S 10.41.

Degree of hydrolysis: B3 = 23.8 %; H3 = 57.5 %; R1 = 110.5%; G0.5 = 64.5 %.

In the same way 6-(D-α-p-chlorobensenesulfonylaminophenylacetamino)-, 6-(D-α-bensenesulfonylamino-phenylacetamino)-, 6-(D-α-p-toluenesulfonylamino-α-(3-thienyl)-acetamido)- and 6-(D-α-o-methoxybensenesulfonylamino-phenylacetamido) penicillanic acid 3-(ethoxy-carbonyloxymethyl)esters were prepared.

EXAMPLE IV

Preparation of 6-(D-α-Benzylsulfonylamino-phenylacetamido) penicillanic acid 3-(1'-cyclopentyloxycarbonyloxyethyl)ester Benzylsulfonylchloride (1.15 g, 6 mM) solved in dry methylenechloride (10 ml) was added dropwise to a stirred and ice-cooled solution of 6-(D-α-amino-phenylacetamido) penicillanic acid 3-(1'-cyclopenthyloxycarbonyloxyethyl)ester (3.04 g, 6 mM) in dry methylenechloride (20 ml). Stirring and cooling was continued for 3 hours. Then the organic layer was washed with cold water, dryed and evaporated. The residue (3.30 g yellowish foam) was chromatographed on silica gel (100 g column with isopropyletheracetone (6:4) mixture. The desired product was isolated as a foam (1.20 g, 30.4 %) and showed only one spot on TLC.

IR (KBr): 1790–1770 ($\beta$-lactam and ester); 1690 (amide).

NMR ($CDCl_3$): 7.30 (s, $C_6H_5$); 7.20 (s, $C_6H_5$); 6.70 (q, OCH($CH_3$)O); 5.90 (s, NH $SO_2$); 5.40 (s, 5-H – 6-H); 5.10 – 4.95 (m, CH in cyclopenthyl, COCH $C_6H_5$); 4.33 (s, 3-H); 4.06 (s, $CH_2SO_2$); 1.75 – 1.40 (m, gem $CH_3$): OCH($CH_3$)O; $CH_2$:s in cyclopenthyl).

Analysis: Calculated for $C_{31}H_{37}N_3O_9S_2$ (659,80): C 56.43; H 5.65; N 6.37; O 21.82; S 9.72.

Found: C 56.72; H 5.70; N 6.25; O 21.45; S 9.68.

Degree of hydrolysis: B3 = 4.8 %; H3 = 15.2 %; R1 = 92.6 %; G 0.5 = 78.5 %.

In the same way 6-(D-$\alpha$-2,5-dichloro-bensenesulfonylamino-phenylacetamido)-, 6-(D-$\alpha$-trichlormethylsulfonylamino-phenylacetamido)-, 6-(D-$\alpha$-p-nitrobensenesulfonylamino-phenylacetamido)-, 6-(D-$\alpha$-3-nitrobenzylsulfonylamino-phenylacetamido)- and 6-($\alpha$-methyl-$\alpha$-benzylsulfonylamino-phenylacetamido) penicillanic acid (3-(1'-ethoxycarbonyloxyethyl)esters were prepared.

EXAMPLE V

Preparation of 6-(D-$\alpha$-Benzylsulfonylamino-phenylacetamido) penicillanic acid 3-(1'-2''-N-benzyloxycarbonylmethylaminoethoxycarbonyloxyethyl)ester From $\alpha$-chloro-$\beta$'-N-benzyloxycarbonylmethylaminoethoxy diethylcarbonate (3.16 g, 10 mM) and 6-(D-$\alpha$-benzylsulfonylaminophenylacetamido) penicillanic acid potassium salt (5.4 g, 10 mM) in dry dimethylsulfoxide (11 ml) the title compound was prepared (0.9 g, 11.5 %) according to the description given in Example III.

The substance showed only one spot on TLC.

IR (KBr): 1780–1760 ($\beta$-lactam and ester); 1690 (amide).

NMR ($CDCL_3$): 7.35 (s, $C_6H_5$); 7.25 (s, $C_6H_5$); 6.75 (q, OCH ($CH_3$)O); 5.95 (s, NH $SO_2$); 5.40 (s, 5-H – 6-H); 5.10 (s, $COOCH_2C_6H_5$); 5.05 (s, CO CH $C_6H_5$); 4.35 (s, 3-H); 4.25 –4.10 (m, $CH_2SO_2$, $OCH_2CH_2N$); 3.55 (t, $OCH_2CH_2N$); 2.95 (s, N($CH_3$)); 1.50 – 1.40 (m, gem $CH_3$, OCH($CH_3$)O).

Analysis: Calculated for $C_{37}H_{42}N_4O_{11}S_2$ (782.93): C 56.76; H 5.41; N 7.16; O 22.48; S 8.19.

Found: C 57.08; H 5.53; N 6.95; O 22.14; S 7.91.

Degree of hydrolysis: B3 = 2.5 %; H3 = 18.4 %; R1 = 124 %; G 0.5 = 92.1 %.

In the same way the 6-(D-$\alpha$-bensenesulfonylamino) analogous ester derivative of the title compound was prepared.

EXAMPLE VI

Preparation of 6-(D-$\alpha$-Benzylsulfonylamino-phenylacetamido) penicillanic acid 3-(1'-2''-methylaminoethoxycarbonyloxyethyl) ester D-mandelate The N-benzyloxycarbonyl derivate of the title compound (390 mg, 0.5 mM), prepared in Example V, was hydrogenated in ethylacetate (16 ml) over palladium charcoal (0.5 g, Pd content 10 %) in the presence of D-mandelic acid (76 mg, 0.5 mM) at room temperature and normal pressure. After 16 hours the catalyst was filtered off and the filtrate evaporated in vacuo. The residue was dissolved in water (5 ml), washed with ether (2 × 5 ml) and the water-phase was freeze-dried (315 mg, 78.5 %). Purity: 91.5 % (iodometric assay).

IR (KBr): 2730–2550 (ammonium); 1790–1765 ($\beta$-lactam and ester); 1680 (amide); 1610 (ammonium).

Degree of hydrolysis: B3 = 27.5 %; H3 = 68.2 %; R1 = 112 %; G 0.5 = 93.5 %.

In the same way the 6-(D-$\alpha$-bensenesulfonylamino) analogous ester derivative of the title compound was prepared.

EXAMPLE VII

Preparation of 6-(D-$\alpha$-Benzylsulfonylamino-phenylacetamido) penicillanic acid 3-(2'-N-bensyloxycarbonylmethylaminoethoxycarbonyloxymethyl)ester From chloromethyl-2-N-benzyloxycarbonyl methylamino ethoxy carbonate (3.02 g, 10 mM) and 6-(D-$\alpha$-benzylsulfonylaminophenylacetamido) penicillanic acid potassium salt (5.4 g, 10 mM) in dry dimethylformamide (25 ml) the title compound was prepared (1.2 g, 15.6 %) according to the description given in Example III.

This substance was uniform according to TLC.

IR (KBr): 1780–1760 ($\beta$-lactam and ester); 1690 (amide).

NMR ($CDCl_3$): 7.35 (s, $C_6H_5$); 7.25 (s, $C_6H_5$); 5.95 (s, $NHSO_2$); 5.70 (s, $OCH_2O$); 5.45 (s, 5-H – 6-H); 5.10 (s, $COOCH_2C_6H_5$); 5.05 (s, COCH $C_6H_5$); 4.35 (s, 3-H); 4.30 – 4.10 (m, $CH_2SO_2$, $OCH_2CH_2N$); 3.60 (t, $OCH_2CH_2N$); 2.95 (s, N($CH_3$)); 1.50 (s, gem $CH_3$).

Analysis: Calculated for $C_{36}H_{40}N_4O_{11}S_2$ (768,90): C 56.24; H 5.24; N 7.29; O 22.89; S 8.34.

Found: C 56.19; H 5.30; N 7.11; O 22.73; S 8.24.

Degree of hydrolysis: B3 = 15.1 %; H3 = 29.5 %; R1 = 113 %; G0.5 = 121 %.

In the same way the 6-(D-$\alpha$-p-toluene sulfonylamino) analogous ester derivative of the title compound was prepared.

EXAMPLE VIII

Preparation of 6-(D-$\alpha$-Benzylsulfonylamino-phenylacetamino) penicillanic acid 3-(2'-methylaminoethoxycarbonyloxymethyl ester salicylate The N-benzyloxycarbonyl derivative of the title compound (310 mg, 0.4 mM), prepared in the previous Example, was hydrogenated in a similar manner as was given in Example VI in the presence of salicylic acid (55 mg, 0.4 mM). After 10 hours the catalyst was filtered off and the filtrate was evaporated to dryness. The residue, a white solid microcrystallin powder, had a purity of 95.7 % (iodometric assay).

IR (KBr): 2800–2580 (ammonium); 1780–1765 ($\beta$-lactam and ester); 1685 (amide); 1605 (ammonium).

Degree of hydrolysis: B3 = 45.8 %; H3 = 85.4 %; R1 = 128 %; G0.5 = 98.2 %.

In the same way the 6-(D-$\alpha$-p-toluenesulfonylamino) analogous ester derivative of the title compound was prepared.

EXAMPLE IX

Preparation of 6-(D-α-Benzylsulfonylamino-phenylacetamido) penicillanic acid 3-(1'-2''-azidoethoxycarbonyloxyethyl)ester From 1'- chloro-2-azido diethylcarbonate (1.9 g, 10 mM) and α-(benzylsulfonylamino)phenylacetamido penicillanic acid potassium salt (5.4 g, 10 mM) in dry dimethylsulfoxide (12 ml) the title compound was prepared (1.7 g, 25.7 %) according to the description given in Example III.

The substance showed only one spot on TLC.

IR (KBr): 2150 (azido); 1780–1760 (β-lactam and ester); 1690 (amide).

NMR ($CDCl_3$): 7.40 (s, $C_6H_5$); 7.25 (s, $C_6H_5$); 6.80 (q, O<u>CH</u> ($CH_3$)O); 5.95 (s, $NHSO_2$); 5.45 (s, 5-H – 6-H); 5.05 (s, CO<u>CH</u>$C_6H_5$); 4.40 (s, 3-H); 4.35 – 4.15 (m, $CH_2SO_2$, O<u>$CH_2$</u>$CH_2N_3$); 3.50 (t, O<u>$CH_2$</u>$CH_2N_3$); 1.60 – 1.40 (m, gem $CH_3$, OCH(<u>$CH_3$</u>)O).

Analysis: Calculated for $C_{28}H_{32}N_6O_9S_2$ (660,76): C 50.90; H 4.88; N 12.72; O 21.79; S 9.71.

Found: C 51.12; H 4.55; N 12.53; O 21.46; S 9.48.

Degree of hydrolysis: B3 = 7.2 %; H3 = 39.5 %; R1 = 99.2 %; G0.5 = 80.6 %.

In the same way the 6-(D-α-o-methoxybensenesulfonylamino) analogous derivative, furthermore the 3-(1'-3''-azidopropoxycarbonyloxyethyl)ester derivative of the title compound were prepared.

EXAMPLE X

Preparation of 6-(D-α-Benzylsulfonylamino-phenylacetamido) penicillanic acid 3-(1'-2''-aminoethoxycarbonyloxyethyl)ester hydrochloride 6-(D-α-Benzylsulfonylamino-phenylacetamido) penicillanic acid 3-(1'-2''-azidoethoxycarbonyloxyethyl)ester (1.3 g, 2 mM) was hydrogenated in an open system in tetrahydrofurane (55 ml) over palladium charcoal (1.2 g, Pd content 10 %) at room temperature, the pH value of the reaction mixture being maintained at 3 by continuous addition of 1 N hydrochloric acid via an automatic titrator. After 3 hours no hydrochloric acid consumption was detectable, the catalyst was filtered off and the filtrate evaporated to dryness in vacuo, the residue was solved in water, extracted with isopropylether several times and freeze-dried. The white hygroscopic residue (820 mg, 61 %) had a purity of 89.2 % (iodometric assay).

IR (KBr): 3050 (ammonium); 1795–1760 (β-lactam and ester); 1695 (amide); 1515 (ammonium).

Degree of hydrolysis: B3 = 19.5 %; H3 = 48.2 %; R1 = 107 %; G0.5 = 88.2 %.

In the same way the 6-(D-α-o-methoxybensene-sulfonylamino) analogous ester derivative, furthermore the 3-(1'-3''-aminopropoxycarbonyloxyethyl)ester derivative of the title compound were prepared.

EXAMPLE XI

Preparation of 6-(D-α-Benzylsulfonylamino-phenylacetamido) penicillanic acid 3-(2'-azidoethoxycarbonyloxymethyl)ester From chloromethyl-2-azidoethylcarbonate (1.8 g, 10 mM) and 6-(D-α-benzylsulfonylamino-phenylacetamido) penicillanic acid potassium salt (5.15 g, 9.5 mM) in dry dimethylsulfoxide (10 ml) the title compound was prepared (1.6 g, 26.0 %) according to the description given in Example III.

The substance showed only one spot on TLC.

IR (KBr): 2150 (azido); 1780–1750 (β-lactam and ester); 1690 (amide).

NMR ($CDCl_3$): 7.35 (s, $C_6H_5$); 7.25 (s, $C_6H_5$); 5.95 (s, $NHSO_2$); 5.80 (s, $OCH_2O$); 5.45 (s, 5-H – 6-H); 5.05 (s, CO<u>CH</u>$C_6H_5$); 4.40 (s, 3-H); 4.30 – 4.10 (m, $CH_2SO_2$, O<u>$CH_2$</u>$CH_2N_3$); 3.50 (t, $OCH_2$<u>$CH_2$</u>$N_3$); 1.45 (s, gem $CH_3$).

Analysis: Calculated for $C_{27}H_{30}N_6O_9S_2$ (646,72): C 50.14; H 4.68; N 13.00; O 22.27; S 9.92.

Found: C 50.35; H 4.88; N 12.65; O 21.84; S 9.65.

Degree of hydrolysis: B3 = 17.8 %; H3 = 33.1 %; R1 = 125 %; G0.5 = 97.5 %.

In the same way the 6-(D-α-p-chlorobenzenesulfonyl-aminophenylacetamino) and the 6-(D-α-p-toluenesulfonylamino-α-(3-thienyl)-acetamido) analogous ester derivatives, furthermore the 3-(3'-azidopropoxycarbonyloxymethyl)- and the 3-(4'-azidobutoxycarbonyloxymethyl)ester derivatives of the title compound were prepared.

EXAMPLE XII

Preparation of 6-(D-α-Benzylsulfonylamino-phenylacetamido) penicillanic acid 3-(2'-acetamido-ethoxycarbonyloxymethyl) ester 6-(D-α-benzylsulfonylamino-phenylacetamido) penicillanic acid 3-(2'-azidoethoxycarbonyloxymethyl)ester (1.29 g. 2 mM) was hydrogenated in dry dioxane (40 ml) over palladium charcoal (1.3 g, Pd content 10 %) in the presence of acetic anhydrid (1.6 g, 16 mM) at room temperature and normal pressure. After 20 hours the catalyst was filtered off and the filtrate was concentrated to 10 ml volume. Water (60 ml) was added and after 3 hours the water phase was extracted with ethylacetate (3 × 25 ml). The organic phase was washed with cold 0.5 N sodium bicarbonate and with cold water. After drying, the organic phase was evaporated to dryness and the residue (1.25 g white foam) was chromatographed on silica gel (50 g) column with ethylacetate. The desired product was isolated as a white foam (0.92 g, 69.5%) and was uniform according to TLC.

IR (KBr): 3050 (ammonium); 1790–1760 (β-lactam and ester); 1690 (amide); 1515 (ammonium).

NMR ($CDCl_3$): 7.35 (s, $C_6H_5$); 7.25 (s, $C_6H_5$); 5.95 (s, $NHSO_2$); 5.82 (s, $OCH_2O$); 5.50 (s, 5-H – 6-H); 5.05 (s, CO<u>CH</u>$C_6H_5$); 4.43 (s, 3-H); 4.35 – 4.05 (m, $CH_2SO_2$, O<u>$CH_2$</u>$CH_2$NH); 3.50 (t, $OCH_2$<u>$CH_2$</u>NH); 1.95 (s, NHCO <u>$CH_3$</u>); 1.50 (s, gem $CH_3$).

Analysis:- Calculated for $C_{29}H_{34}N_4O_{10}S_2$ (662.76): C 52.56; H 5.17; N 8.45; O 24.14; S 9.68.

Found: C 52.76; H 5.25; N 8.32; O 24.02; S 9.72.

Degree of hydrolysis: B3 = 52.8 %; H3 = 82.6 %; R1 = 108 %; G0.5 = 88.2 %.

EXAMPLE XIII

Preparation of 6-(D-α-Benzylsulfonylamino-phenylacetamido) pencicillanic acid 3-(ethoxycarbonylaminomethyl)ester From chloromethylaminoethoxy carbonate (0.96 g, 7 mM) and 6-(D-α-benzylsulfonylaminophenylacetamido) penicillanic acid potassium salt (3.8 g, 7 mM) in dry dimethyl formamide (25 ml) the title compound was prepared (0.9 g, 21.5 %) according to the description given in Example III.

This substance was uniform according to TLC.

IR (KBr): 1790 (β-lactam and ester); 1720–1690 (amide).

NMR ($CDCl_3$): 7.35 (s, $C_6H_5$); 7.25 (s, $C_6H_5$); 6.00 (s, $NHSO_2$); 5.50 (s, 5-H - 6-H); 5.05 (s, $CO\underline{C}HC_6H_5$); 4.75 (d, $O\underline{CH_2}$ NH); 4.40 – 4.00 (m, 3-H, $CH_2SO_2$, $O\underline{C}H_2CH_3$); 1.50 – 1.15 (m, gem $CH_3$, $OCH_2\underline{CH_3}$).

Analysis: Calculated for $C_{27}H_{32}N_4O_8S_2$ (604,73): C 53.63; H 5.33; N 9.27; O 21.17; S 10.61.

Found: C 53.88; H 5.38; N 9.18; O 20.98; S 10.52.

Degree of hydrolysis: B3 = 1.8 %; H3 = 5.2 %; R1 = 52.4 %; G0.5 = 61.5 %.

In the same way 6-(D-α-o-methoxybenzenesulfonylamino-) and 6-(D-α-benzenesulfonylamino-phenylacetamido) analogous derivatives were prepared.

EXAMPLE XIV

Preparation of 6-(D-α-Benzylsulfonylamino-phenylacetamido) penicillanic acid 3-(cis-2-methyl-1,3-dioxanyl-5-oxycarbonyloxy methyl)ester From chloromethyl-cis-2-methyl-1,3-dioxanyl-5-oxy carbonate (2.9 g, 13.5 mM) and 6-(D-α-benzylsulfonylamino-phenylacetamido) penicillanic acid sodium salt (7.1 g, 13.5 mM) in dry dimethyl formamide (40 ml) the title compound was prepared (1.61 g, 17.6%) according to the description given in Example III.

IR (KBr): 1780–1760 (β-lactam and ester); 1690 (amide).

NMR ($CDCl_3$): 7.40 (s, $C_6H_5$); 7.30 (s, $C_6H_5$); 5.95 (s, $NHSO_2$); 5.83 (s, $OCH_2O$); 5.50 (s, 5-H - 6-H); 5.05 (s, $CO\underline{CH}$ $C_6H_5$); 4.75 (q, $\underline{CH}CH_3$); 4.50 (m, OCOO $\underline{CH}$); 4.43 (s, 3-H); 4.20 – 4.00 (m, $CH_2SO_2$; $CH_2$:s in dioxanyl); 1.50 – 1.30 (m, gem $CH_3$; CH $\underline{CH_3}$).

Analysis: Calculated for $C_{30}H_{35}N_3O_{11}S_2$ (677.77): C 53.16; H 5.21; N 6.20; O 25.97; S 9.46.

Found: C 53.38; H 5.26; N 6.08; O 25.72; S 9.28.

Degree of hydrolysis: B3 = 11.8 %; H3 = 23.6 %; R1 = 91.8 %; G0.5 = 73.5 %.

In the same way the 3-(1'-2 methyl-1,3-dioxanyl-5-oxycarbonyloxyethyl) analogous ester derivative was prepared.

EXAMPLE XV

Preparation of 6-(D-α-Acetylureido-phenylacetamido) penicillanic acid 3-(1'-ethoxycarbonyloxyethyl)ester To a stirred and ice-cooled solution of 6-(D-α-amino-phenylacetamido) penicillanic acid 3-(1'-ethoxycarbonyloxyethyl)ester (1.0 g, 2.0 mM) in dry methylene chloride (5 ml) acetylisocyanate (0.16 g, 1.8 mM) in dry methylene chloride (3 ml) was added. Stirring was continued for 1 hour, then the organic layer was washed with 5 ml cold water, dryed and evaporated. The residue (1.1 g white foam) was chromatographed on silica gel (55 g) column with isopropylether-acetone (6:4) mixture. The desired product was isolated as a foam (0.9 g, 82 %) and showed only one spot on TLC.

IR (KBr): 1780–1760 (β-lactam and ester); 1700–1680 (amide).

NMR ($CDCl_3$): 7.35 (s, $C_6H_5$); 6.80 (q, $O\underline{CH}$($CH_3$)O); 5.90 (s, $CO\underline{CH}C_6H_5$); 5.40 (s, 5-H - 6-H); 4.35 (s, 3-H); 4.25 (q, $O\underline{CH_2}CH_3$); 2.10 (s, NH CO $\underline{CH_3}$); 1.60 – 1.20 (m, gem $CH_3$, OCH($\underline{CH_3}$)O, $OCH_2\underline{CH_3}$).

Analysis: Calculated for $C_{24}H_{30}N_4O_9S$ (550.60): C 52.35; H 5.49; N 10.18; O 26.15; S 5.83.

Found: C 52.55; H 5.56; N 9.98; O 25.95; S 5.68.

Degree of hydrolysis: B3 = 7.4 %; H3 = 33.2 %; R1 = 90.4 %; G 0.5 = 71.1%.

In the same way the 6-(D-α-p-chlorobenzoyl-thioureido-), 6-(D-α-benzoylureido-), 6-(O-α-o-methoxybenzoylureido-) and 6-(D-α-benzene-sulfonylureido-phenylacetamido) analogous ester derivatives of the title compound were prepared.

EXAMPLE XVI

Preparation of 6-(D-α-Acetylureido-phenylacetamido) penicillanic acid 3-(1'-cyclopenthylcarbonyloxyethyl)ester From α-chloroethyl cyclopenthyl carbonate (4.3 g, 20 mM) and 6-(D-α-acetylureido-phenylacetamido) penicillanic acid sodium salt (9.15 g, 20 mM) in dry dimethylsulfoxide (13 ml) the title compound was prepared (3.7 g, 31.4 %) according to the description given in Example III. The substance showed only one spot on TLC.

IR (KBr): 1780–1760 (β-lactam and ester); 1690 (amide).

NMR ($CDCl_3$): 7.40 (s, $C_6H_5$); 6.85 (q, $O\underline{CH}$($CH_3$)O); 5.95 (s, CO $\underline{CH}$ $C_6H_5$); 5.45 (s, 5-H - 6-H); 5.20 – 5.05 (m, CH in cyclopenthyl); 4.33 (s, 3-H); 2.15 (s, NH CO $\underline{CH_3}$); 1.85 – 1.40 (m, gem $CH_3$, OCH($\underline{CH_3}$)O, $CH_2$:s in cyclopenthyl).

Analysis: Calculated for $C_{27}H_{34}N_4O_9S$ (590.67): C 54.90; H 5.80; N 9.49; O 24.38; S 5.43.

Found: C 54.24; H 5.96; N 8.61; O 23.22; S 4.71.

Degree of hydrolysis: B3 = 5.1 %; H3 = 22.8 %; R1 = 96.5 %; G0.5 = 64.4 %.

In the same way the 3-(ethoxycarbonyloxymethyl), 3-(phenoxycarbonyloxymethyl) and the 3-(2'-azidoethoxycarbonyloxymethyl) analogous ester derivatives of the title compound were prepared.

EXAMPLE XVII

Preparation of 6-(D-α-Acetylureido-phenylacetamido) penicillanic acid 3-(1'-phenoxycarbonyloxyethyl)ester 6-(D-α-acetylureido-phenylacetamido) penicillanic acid sodium salt (9.15 g, 20 mM) was added to a stirred and ice-cooled mixture of tetrabutylammoniumhydrogen sulfate (6.8 g, 20 mM), sodium hydroxide (10 ml, 2 M solution), water (10 ml) and chloroform (20 ml). pH was kept at 7,5 with tetrabutylammoniumhydrogen sulfate. The organic phase was separated, dried and α-chloroethylphenyl carbonate (5.1 g, 25 mM) was added. The reaction mixture was stirred at 40°C for 16 hours.

Water (100 ml) and ether (100 ml) were added and the organic layer was washed successively with 0.5 N sodium bicarbonate solution and water. After drying the organic phase was evaporated to dryness and the yellow oil (4.9 g) was chromatographed on silica gel (100 g) column with isopropylether-aceton (6:4) mixture. The desired product was isolated as a foam (1.0 g, 8.4%) and it showed only one spot on TLC.

IR (KBr): 1790–1780 (β-lactam and ester); 1690 (amide).

NMR ($CDCl_3$): 7.36 (s, $C_6H_5$); 6.85 (q, $O\underline{CH}$($CH_3$)O); 5.90 (s, $CO\underline{CH}$ $C_6H_5$); 5.40 (s, 5-H - 6-H); 4.33 (s. 3-H); 2.10 (s, $NHCO\underline{CH_3}$); 1.65 – 1.40 (m, gem $CH_3$, $OCH(\underline{CH_3})O$).

Analysis: Calculated for $C_{98}H_{30}N_4O_9S$ (598.65): C 56.18; H 5.05; N 9.36; O 24.05; S 5.36.

Found: C 56.33; H 5.19; N 9.14; O 23.94; S 5.16.

Degree of hydrolysis: B3 = 5.9 %; H3 = 25.7 %; R1 = 92.5 %; G0.5 = 65.6 %.

In the same way the 3-(1'-ethoxycarbonyloxyethyl) and 3-(1'-phenoxycarbonyloxyethyl) analogous ester derivatives of the title compounds were prepared.

EXAMPLE XVIII

Preparation of 6-(D-α-Furylureido)-phenylacetamido)penicillanic acid 3-(1'-ethoxycarbonyloxyethyl)ester From 6-(D-α-amino-phenylacetamido) penicillanic acid 3-(1'-ethoxycarbonyloxyethyl)ester (2.0 g, 4.0 mM) and α-furylisocyanate (0.50 g, 3.7 mM) in dry methylene chloride (15 ml) the title compound was prepared (1.5 g, 67.5 %) according to the description given in Example XI.

This substance was uniform according to TLC.

IR (KBr): 1790–1770 (β-lactam and ester); 1690 (amide).

NMR ($CDCl_3$): 7.60 - 7.35 (m, 3-H - 4-H in furyl); 7.35 (s, $C_6H_5$); 6.80 (q, $O\underline{CH}(CH_3)O$); 6.60 - 6.50 (m, 5-H in furyl); 5.90 (s, $CO\underline{CH}$ $C_6H_5$); 5.40 (s, 5-H - 6-H); 4.35 (s, 3-H); 4.20 (q, $O\underline{CH_2}CH_3$); 1.55 - 1.15 (m, gem $CH_3$, $OCH(\underline{CH_3})O$, $OCH_2\underline{CH_3}$).

Analysis: Calculated for $C_{27}H_{30}N_4O_{10}S$ (602.63): C 53.81; H 5.02; N 9.30; O 26.55; S 5.32.

Found: C 54.16; H 5.12; N 9.03; O 26.32; S 5.14.

Degree of hydrolysis: B3 = 8.10 %; H3 = 19.5 %; R1 = 79.8 %; G0.5 = 66.0 %.

In the same way the 3-(ethoxycarbonyloxymethyl), 3-(1'-phenoxycarbonyloxyethyl) and 3-(phenoxycarbonyloxymethyl) analogous ester derivatives were prepared.

Example XIX

Preparation of 6-(D-α-(3-Guanyl-1-ureido)-phenylacetamido) penicillanic acid 3-(1'-ethoxycarbonyloxyethyl)ester hydrochloride Sodium nitrite (0.69 g, 10 mM) in water (5 ml) was added to a stirred ice-cooled solution of 3-guanyl-1-ureido dihydrochloride (1.9 g, 10 mM) in water (20 ml). After stirring at 0°C for 10 minutes the mixture was slowly added to an ice-cooled solution of 6-(D-α-amino-phenylacetamido) penicillanic acid 3-(1'-ethoxycarbonyloxyethyl)ester (5.0 g, 10 mM) in 90 % tetrahydrofuran (50 ml). pH was kept at 7.5 with solid potassium bicarbonate. After stirring and cooling for 1.5 hours the tetrahydrofuran was evaporated, ethylacetate was added and the pH was adjusted to 9.0 with potassium bicarbonate. The organic phase was dried and extracted with hydrochloric acid.

The water phase was extracted with isopropylether and freeze-dried.

The freeze-dried product (0.63 g, 10.8 %, purity: 89.5 %) showed one main spot on TLC and the IR spectrum (KBr) of the compound exhibited strong bands around 1780–1760 (β-lactam and ester) and 1690 (amide).

NMR (dimethylsulfoxide): 7.55 (s, $C_6H_5$); 6.80 (q, $O\underline{CH}(CH_3)O$); 5.50 (s, 5-H - 6-H); 4.40 (s, 3-H); 4.25 (q, $O\underline{CH_2}CH_3$); 1.60 - 1.15 (m, gem $CH_3$, $OCH(\underline{CH_3})O$, $OCH_2\underline{CH_3}$).

Degree of hydrolysis: B3 = 9.2 %; H3 = 43.8 %; R1 = 76.1 %; G0.5 = 58.1 %.

In the same way the 3-(1'-phenoxycarbonyloxyethyl) analogous ester derivative was prepared.

EXAMPLE XX

Preparation of 6-(D-α-Hydroxyphenylphosphinylamino-phenylacetamido) penicillanic acid 3-(1'-cyclopenthyloxycarbonyloxyethyl)ester sodium salt

*a.* From benzyloxyphenyl phosphinyl chloride (4.00 g, 15 mM) and 6-(D-α-amino-phenylacetamido) penicillanic acid 3-(cyclopenthyloxycarbonyloxyethyl)ester (7.60 g, 15 mM) was 6-[D-α-(benzyloxyphenyl phosphinyl amino)-phenylacetamido] penicillanic acid 3-(1'-cyclopenthyloxycarbonyloxyethyl)ester (3.58 g, 32.5 %) prepared according to the description given in Example IV.

IR (KBr): 1780–1770 (β-lactam and ester); 1690 (amide).

NMR ($CDCl_3$): 7.35 (s, $C_6H_5$); 7.25 (s, $C_6H_5$); 6.85 (q, $O\underline{CH}(CH_3O)$; 5.45 (s, 5-H - 6-H); 5.20 - 5.10 (m, CH in cyclopenthyl); 5.05 (s, $CO\underline{CH}$ $C_6H_5$); 4.95 (s, $O\underline{CH_2}$ $C_6H_5$); 4.35 (s, 3-H); 1.85 - 1.30 (m, gem $CH_3$; $OCH(\underline{CH_3})O$; $CH_2$:s in cyclopenthyl).

Analysis: Calculated for $C_{37}H_{42}N_3O_9P$ S (735.82): C 60.40; H 5.75; N 5.71; O 19.57; S 4.36.

Found: C 60.65; H 5.82; N 5.62; O 19.04; S 4.14.

*b.* This product was dissolved in ethylacetate (80 ml) and was hydrogenated at room temperature and normal pressure over palladium charcoal (1.75 g, Pd content 5 %) until one equivalent of hydrogen had been absorbed. The catalyst was filtered off, water (50 ml) was added, the pH was adjusted to 7.8 with 2 N sodium hydroxide and the separated water phase was extracted with isopropylether (2 × 50 ml). The sodium salt, obtained from the water phase after freeze-drying, was isolated (2.68 g, 80.5 %). Purity: 88,5 % (iodometric assay).

IR: 1790–1780 (β-lactam and ester); 1690 (amide).

NMR (dimethyl sulfoxide): 7.35 (s, $C_6H_5$); 7.25 (s, $C_6H_5$); 6.85 ($O\underline{CH}(CH_3)O$); 5.40 (s, 5-H - 6-H); 5.20 - 5.10 (m, CH in cyclopenthyl); 5.05 (s, $CO\underline{CH}$ $C_6H_5$); 4.35 (s, 3-H); 1.85 - 1.40 (m, gem $CH_3$, $OCH(\underline{CH_3})O$, $CH_2$:s in cyclopenthyl).

Degree of hydrolysis: B3 = 9.2 %; H3 = 26.6 %; R1 = 97.5 %; G0.5 = 58.2 %.

In the same way the 6-(D-α-hydroxymethoxyphosphinylaminophenylacetamido) penicillanic acid 3-(1'-ethoxycarbonyloxyethyl) and 3-(cyclopenthyloxycarbonyloxymethyl)esters were prepared.

EXAMPLE XXI

Preparation of 6-(D-α-Sulfoamido-phenylacetamido) penicillanic acid 3-(1'-ethoxycarbonyloxyethyl)ester sodium salt To a stirred and ice-cooled solution of 6-(D-α-amino-phenylacetamido) penicillanic acid 3-(1'-ethoxycarbonyloxyethyl)ester (4.0 g, 8 mM) in dry methylene chloride (10 ml) was added trimethylene amino sulfurtrioxide (1.1 g, 8 mM) in small portions over 20 minutes. Stirring was continued with cooling for 1 hour and at room temperature for one more hour. Dry ethylacetate was added and the solution was concentrated to 10 ml, this procedure was repeated twice. To the ethylacetate phase sodium-2-ethylhexanoat (8 mM in methyl isobutyl keton) was added and the mixture was added to an excess of n-hexan. The desired product was formed as white crystals (3.3 g, 72.5 %, purity: 72.8 %) and was uniform according to TLC.

IR (KBr): 1780–1750 (β-lactam and ester); 1680 (amide).

NMR (dimethylsulfoxide): 7.35 (s, $C_6H_5$); 6.75 (q, O<u>CH</u>($CH_3$)O); 5.50 (s, 5-H – 6-H); 5.05 (s, CO <u>CH</u> $C_6H_5$); 4.40 (s, 3-H); 4.30 (q, O<u>CH₂</u>$CH_3$); 1.60 – 1.10 (m, gem $CH_3$, OCH(<u>$CH_3$</u>)O, $OCH_2$<u>$CH_3$</u>).

Degree of hydrolysis: B3 = 13.2 %; H3 = 36.8%; R1 = 109 %; G0.5 = 93.5 %.

In the same way the 3-(1'-cyclopentyoxy-carbonyloxyethyl) and the 3-(phenoxycarbonyloxymethyl) analogous ester derivatives of the title compounds were prepared.

Example XXII

Preparation of 6-(α-Sulfo-phenylacetamido) penicillanic acid 3-(1'-ethoxycarbonyloxyethyl)ester sodium salt To a stirred mixture of 6-amino penicillanic acid 3-(1'-ethoxycarbonyloxyethyl)ester p-toluene sulphonate (13.1 g, 26 mM) and dry triethylamine(4.8 g, 48 mM) in dry chloroform (100 ml) was added dropwise α-sulfophenylacetyl chloride (4.7 g, 20 mM) at −5°C. Stirring was continued for 40 minutes. Water was added (20 ml), the two layers were separated, the organic phase was washed with 0.05 N hydrochloric acid and water. The organic phase was dried and extracted with 0.5 N sodium bicarbonate solution (36 ml). The water phase was extracted with isopropylether and the isopropylether-free water phase was freeze-dried.

The IR spectrum (KBr) of the freeze-dried substance (7.6 g, 60.5 %, purity: 65.3 %) exhibited strong bands around 1780–1760 $cm^{-1}$ (β-lactam and ester) and 1690 $cm^{-1}$ (amide).

NMR (dimethylsulfoxide): 7.50 (s, $C_6H_5$); 6.80 (q, O<u>CH</u>($CH_3$)O); 5.50 (s, 5-H – 6-H); 4.95 (s, CO<u>CH</u>-($SO_2$)$C_6H_5$); 4.40 (s, 3-H); 4.30 (q, O<u>$CH_2$</u> $CH_3$); 1.60 – 1.05 (m, gem $CH_3$, OCH(<u>$CH_3$</u>)O, $OCH_2$<u>$CH_3$</u>).

Degree of hydrolysis: B3 = 13.8 %; H3 = 24.2 %; R1 = 97 %; G0.5 = 66.5 %.

In the same way the 3-(1'-phenoxycarbonyloxyethyl) and the 3-(ethoxycarbonyloxymethyl) analogous ester derivatives were prepared.

EXAMPLE XXIII

Preparation of 6-(α-Tetrazolyl)phenylacetamido) penicillanic acid 3-(1'-ethoxycarbonyloxyethyl)ester sodium salt To a stirred mixture of 6-aminopenicillanic acid 3-(1'-ethoxycarbonyloxyethyl)ester p-toluenesulphonate (4.10 g, 8 mM) and dry triethylamine (1.6 g, 16 mM) in dry methylene chloride (25 ml) was added p-nitrophenyl α-(5-tetrazolyl)-phenylacetate (2.44 g, 7.5 mM) at −5°C. Stirring was continued for 2 hours, the cooling bath was then removed and stirring was continued for 24 hours at room temperature. It was then added to ice-water with stirring and the layers were separated. The organic phase was washed with water, 0.05 N hydrochloric acid and water. The organic phase was then dried and was treated with 16 mM of a 50 % solution of sodium 2-ethylhexanoate in n-butane. Upon evaporation of the solvent to a minimum amount a yellow solid separated, which was triturated and filtered off with ether (2.38 g, 64.5 %). Purity: 87.5 % (iodometric assay).

IR (KBr): 1780–1760 (β-lactam and ester); 1690 (amide).

NMR (dimethylsulfoxide): 7.50 (s, $C_6H_6$); 6.75 (q, O<u>CH</u>($CH_3$)O); 5.70 (s, CO<u>CH</u> $C_6H_5$); 5.50 (s, 5-H – 6-H); 4.40 (s, 3-H); 4.25 (q, O<u>$CH_2$</u>$CH_3$); 1.60 – 1.10 (m, gem $CH_3$, OCH(<u>$CH_3$</u>)O, $OCH_2$<u>$CH_3$</u>).

Degree of hydrolysis; B3 = 1.2 %; H3 = 14.5 %; R1 = 69.5 %; G0.5 = 77 %.

In the same way the 3-(phenoxycarbonyloxymethyl) analogous ester derivative was prepared.

EXAMPLE XXIV

Pharmaceutical formulations

For preparation of tablets the following compositions were made:

| | | |
|---|---|---|
| a) | 1'-Ethoxycarbonyloxy-ethyl 6-(D-α-benzyl-sulphonylamino-phenylacetamido)penicillanate | 350 mg |
| | Starch | 100 mg |
| | Magnesium stearate | 10 mg |
| b) | 1'-Ethoxycarbonyloxyethyl 6-(α-benzylsulphonyl-amino-3-thienyl-acetamido)penicillanate | 350 mg |
| | Starch | 100 mg |
| | Magnesium stearate | 10 mg |
| c) | Ethoxycarbonyloxymethyl 6-(D-α-benzylsulphonyl-aminophenylacetatamido)penicillanate | 400 mg |
| | Calcium carbonate | 100 mg |
| | Magnesium stearate | 10 mg |
| d) | 1'-Aminoethoxycarbonyloxymethyl 6-(D-α-benzyl-sulphonylaminophenylacetamido)penicillinate hydrochloride | 400 mg |
| | Lactose | 100 mg |
| | Magnesium stearate | 10 mg |
| e) | 1'-Ethoxycarbonyloxyethyl 6-(D-α-acetylureido-phenylacetamido)penicillanate | 400 mg |
| | Microcrystalline cellulose (Avicel) | 100 mg |
| | Magnesium stearate | 10 mg |
| f) | 1'-Cyclopentyloxycarbonyloxyethyl 6-(D-α-acetyl-ureidophenylacetamido)penicillanate hydro-chloride | 350 mg |
| | Calcium carbonate | 100 mg |
| | Lactose | 100 mg |
| | Magnesium stearate | 10 mg |
| g) | 1'-Ethoxycarbonyloxy-ethyl 6-(-α-hydroxysulphonyl-phenylacetamido)penicillanate sodium salt | 400 mg |
| | Starch | 100 mg |
| | Magnesium stearate | 10 mg |

For filling in capsules the following formulations were made:

| | | |
|---|---|---|
| h) | 1'Ethoxycarbonyloxy-ethyl 6-(D-α-2-furoyl-ureidophenylacetamido)penicillanate | 350 mg |
| | Magnesium stearate | 5 mg |
| i) | 1'-Ethoxycarbonyloxyethyl 6-(Dα-(hydroxy)phenylphosphinylaminophenylacetamido)penicillanate sodium salt | 400 mg |
| | Lactose | 40 mg |
| | Magnesium stearate | 5 mg |

For oral suspensions the following formulations were prepared:

| | | |
|---|---|---|
| j) | 1'-Ethoxycarbonyloxyethyl 6-(D-α-sulphoamino-phenylacetamido)penicillanate sodium salt | 35 mg |
| | Aluminium monostearate | 50 mg |
| | Tween - 80 | 1.2 mg |
| | Peanut oil | ad 1000 mg |
| k) | 1'-Ethoxycarbonyloxyethyl 6-(α-5-tetrazolyl-phenylacetamido)penicillanate | 35 |
| | Sodium benzoate | 0.48 |
| | Sodium chloride | 0.75 |
| | Flavouring agents | 4.7 |
| | Aerosil | 0.3 |
| | Antifoam | 0.0375 |
| | Alkali salts of polysaccharide sulphates | 4.0 |
| | Sodium saccharinate | 0.4 |
| | Sorbitol | ad 100 |

We claim:

1. A pharmaceutical preparation for the treatment of diseases caused by bacterial organisms wherein the active ingredient is an anti-bacterially effective amount of the compound 1'-ethoxycarbonyloxyethyl 6-(D-α-benzylsulphonylamino-phenyl-acetamido)-penicillanate or a therapeutically acceptable salt thereof in association with a pharmaceutically acceptable carrier, wherein the amount of active ingredient is in the range of about 1%–95%.

2. A capsule or tablet suitable for oral administration for the treatment of diseases caused by bacterial organisms containing therein a pharmaceutical preparation according to claim 1.

3. A pharmaceutical preparation for the treatment of diseases caused by bacterial organisms wherein the active ingredient is an anti-bacterially effective amount of the compound ethoxycarbonyloxymethyl 6-(D-α-benzylsulphonylamino-phenylacetamido)penicillanate or a therapeutically acceptable salt thereof in association with a pharmaceutically acceptable carrier, wherein the amount of active ingredient is in the range of about 1%–95%.

4. A capsule or tablet suitable for oral administration for the treatment of diseases caused by bacterial organisms containing therein a pharmaceutical preparation according to claim 3.

5. A method for treatment of diseases caused by bacterial organisms in animals, including man, comprising administering to a host an antibacterially effective amount of the compound 1'-ethoxycarbonyloxyethyl 6-(D-α-benzylsulphonylamino-phenylacetamido)-penicillanate or a therapeutically acceptable salt thereof.

6. A method for treatment of diseases caused by bacterial organisms in animals, including man, comprising administering to a host an antibacterially effective amount of the compound ethoxycarbonyloxymethyl 6-(D-α-benzylsulphonylamino-phenylacetamido)-penicillanate or a therapeutically acceptable salt thereof.

* * * * *